United States Patent
Dunn et al.

(10) Patent No.: US 10,472,493 B2
(45) Date of Patent: Nov. 12, 2019

(54) HYDROLYTICALLY STABLE POLYMER COMPOSITIONS, ARTICLES, AND METHODS

(71) Applicant: Medtronic, Inc., Minneapolis, MN (US)

(72) Inventors: Patricia E. Dunn, Minneapolis, MN (US); Ronald A. Drake, St. Louis Park, MN (US); Xiangji Chen, Plymouth, MN (US); Samuel E. Owings, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 2 days.

(21) Appl. No.: 15/498,146

(22) Filed: Apr. 26, 2017

(65) Prior Publication Data
US 2017/0313853 A1 Nov. 2, 2017

Related U.S. Application Data

(60) Provisional application No. 62/328,742, filed on Apr. 28, 2016.

(51) Int. Cl.
| | | |
|---|---|---|
| C08K 5/29 | (2006.01) | |
| A61L 29/06 | (2006.01) | |
| C08K 3/14 | (2006.01) | |
| C08K 5/3435 | (2006.01) | |

(52) U.S. Cl.
CPC .............. *C08K 5/29* (2013.01); *A61L 29/06* (2013.01); *C08K 3/14* (2013.01); *C08K 5/3435* (2013.01)

(58) Field of Classification Search
None
See application file for complete search history.

(56) References Cited

U.S. PATENT DOCUMENTS

| | | | |
|---|---|---|---|
| 4,520,171 A | 5/1985 | Diveley et al. | |
| 4,987,168 A | 1/1991 | Kerschbaumer | |
| 5,360,888 A | 11/1994 | Ullrich | |
| 5,668,198 A | 9/1997 | Suhadolnik et al. | |
| 8,147,769 B1 | 4/2012 | Huang et al. | |
| 9,045,480 B2 | 6/2015 | Schoning et al. | |
| 2005/0004294 A1 | 1/2005 | Chin et al. | |
| 2007/0066727 A1 | 3/2007 | Denzinger et al. | |
| 2008/0033080 A1 | 2/2008 | Mader et al. | |
| 2008/0242783 A1* | 10/2008 | Ganesan | C08G 63/19 524/413 |
| 2008/0293841 A1 | 11/2008 | Andrew et al. | |
| 2009/0018633 A1 | 1/2009 | Lindquist et al. | |
| 2011/0092620 A1 | 4/2011 | Scheffner et al. | |
| 2012/0083557 A1 | 4/2012 | Schoening | |
| 2013/0078402 A1* | 3/2013 | Mitadera | C08G 69/26 428/36.9 |
| 2014/0243875 A1* | 8/2014 | Chen | B29C 47/0023 606/194 |
| 2017/0130046 A1* | 5/2017 | Ohashi | C08K 5/04 |
| 2018/0334593 A1* | 11/2018 | Shiga | B32B 27/08 |

FOREIGN PATENT DOCUMENTS

| | | |
|---|---|---|
| WO | 2011153184 | 12/2011 |

OTHER PUBLICATIONS

Product Data Sheet, Stabilizer 9000.*
Product Information Sheet for Tinuvin 622, Mar. 24, 2014, p. 1-8.*
https://www.rheinchemie.com/content/uploads/2014/07/stabaxol_brochure_en_120330_online1.pdf.
(PCT/US2017/029694) PCT Notification of Transmittal of the International Search Report and the Written Opinion of the International Searching Authority, dated Sep. 20, 2017, 13 pages.

* cited by examiner

*Primary Examiner* — Robert T Butcher

(57) ABSTRACT

A composition, article, and method for increasing the hydrolytic stability of a polymer; wherein a composition includes: a polymer comprising functional groups having hydrolyzable bonds; a carbodiimide compound; and a weak base (or hindered amine); wherein the carbodiimide compound and weak base (or hindered amine) are used in amounts effective to decrease the rate and/or extent of hydrolytic degradation of the polymer relative to either used alone in the same amount with the polymer.

17 Claims, 10 Drawing Sheets

HYDROLYTICALLY STABLE POLYMER COMPOSITIONS, ARTICLES, AND METHODS

BACKGROUND

Polymers degrade over time. Molecular composition, processing, storage, and use conditions are all factors that can affect the degradation rate. For example, the hydrolytic degradation rate of a polyether block amide copolymer has been found to increase when tungsten carbide is added to make radiopaque tips for catheters. Such catheter material degradation can limit shelf life and increase costs. Methods and additives that extend the shelf life of hydrolytically unstable polymers are therefore needed.

SUMMARY

The present disclosure provides polymer compositions, articles, and methods.

The polymer compositions include additives that provide more hydrolytic stability to a polymer than the polymer without the additives. Polymer compositions described herein are particularly suitable for use in at least a portion of a medical device.

In one embodiment, there is provided a composition that includes: a polymer with functional groups having hydrolyzable bonds; a carbodiimide compound; and a weak base other than the carbodiimide compound; wherein the carbodiimide compound and weak base are used in amounts effective to decrease the rate and/or extent of hydrolytic degradation of the polymer relative to either used alone in the same amount with the polymer.

In one embodiment, there is provided a composition that includes: a polymer with functional groups having hydrolyzable bonds; a carbodiimide compound; and a hindered amine; wherein the carbodiimide compound and hindered amine are used in amounts effective to decrease the rate and/or extent of hydrolytic degradation of the polymer relative to either used alone in the same amount with the polymer.

Articles are provided in the present disclosure.

In one embodiment, there is provided an article that includes a polymer composition of the present disclosure.

Methods of increasing the hydrolytic stability of a polymer are provided in the present disclosure.

In one embodiment, there is provided a method for increasing the hydrolytic stability of a polymer including functional groups having hydrolyzable bonds. The method includes: providing the polymer; and combining the polymer with a carbodiimide compound and a weak base other than the carbodiimide compound to form a composition; wherein the carbodiimide compound and weak base are used in amounts effective to decrease the rate and/or extent of hydrolytic degradation of the polymer relative to either used alone in the same amount with the polymer.

In one embodiment, there is provided a method for increasing the hydrolytic stability of a polymer including functional groups having hydrolyzable bonds. The method includes: providing the polymer; and combining the polymer with a carbodiimide compound and a hindered amine to form a composition; wherein the carbodiimide compound and hindered amine are used in amounts effective to decrease the rate and/or extent of hydrolytic degradation of the polymer relative to either used alone in the same amount with the polymer.

Herein, "composition" or "polymer composition" refers to the formulation upon initial combination of the components (e.g., polymer, carbodiimide compound, and weak base, or polymer, carbodiimide compound, and hindered amine), prior to being processed (e.g., extruded or otherwise exposed to heat), as well as to an intermediate formed during processing, and to a final product (e.g., at least a portion of an article such as a medical article).

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries. The term "copolymer" refers to a polymer that includes two or more different monomeric units, thereby including terpolymers, tetrapolymers, etc.

A polymer is a molecule that consists of more than 10 monomer units. The term "oligomer" is a molecule that consists of 2 to 10 monomer units, including dimer, trimer, tetramer, pentamer, etc.

Herein, a "weak base" means a chemical that can accept protons but does not fully ionize in aqueous solution, or a chemical base in which protonation is incomplete.

As used herein, the term "organic group" means a hydrocarbon group (with optional elements other than carbon and hydrogen, such as oxygen, nitrogen, sulfur, and silicon) that is classified as an aliphatic group, cyclic group, or combination of aliphatic and cyclic groups (e.g., alkaryl and aralkyl groups). The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group (e.g., the aryl group has at least one aromatic ring and optionally one or more additional rings that can be unsaturated, partially saturated, saturated, or aromatic, wherein one or more of the optional groups may be fused to the aromatic ring) and includes phenyl, naphthyl, biphenyl, phenanthryl, and anthracyl. The term "heterocyclic group" means a closed ring hydrocarbon in which one or more of the atoms in the ring is an element other than carbon (e.g., nitrogen, oxygen, sulfur, etc.). A group that may be the same or different is referred to as being "independently" something.

The term "alkoxy" refers to a monovalent group having an oxy group bonded directly to an alkyl group. The term "aryloxy" refers to a monovalent group having an oxy group bonded directly to an aryl group.

The term "aralkyl" refers to a monovalent group that is an alkyl group substituted with an aryl group (e.g., as in a benzyl group). The term "alkaryl" refers to a monovalent group that is an aryl substituted with an alkyl group (e.g., as in a tolyl group).

The term functional group that includes a "hydrolyzable bond" refers to a group that can react with water having a pH of 1 to 10 under conditions of atmospheric pressure. Such functional groups are often converted to two separated functional groups after reacting with water.

The terms "comprises" and "includes" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The term "in the range" or "within a range" (and similar statements) includes the endpoints of the stated range.

Reference throughout this specification to "one embodiment," "an embodiment," "certain embodiments," or "some embodiments," etc., means that a particular feature, configuration, composition, or characteristic described in connection with the embodiment is included in at least one embodiment of the invention. Thus, the appearances of such phrases in various places throughout this specification are not necessarily referring to the same embodiment of the invention. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DRAWINGS

The disclosure may be more completely understood in connection with the following drawings.

DETAILED DESCRIPTION OF ILLUSTRATIVE EMBODIMENTS

Figure 1:
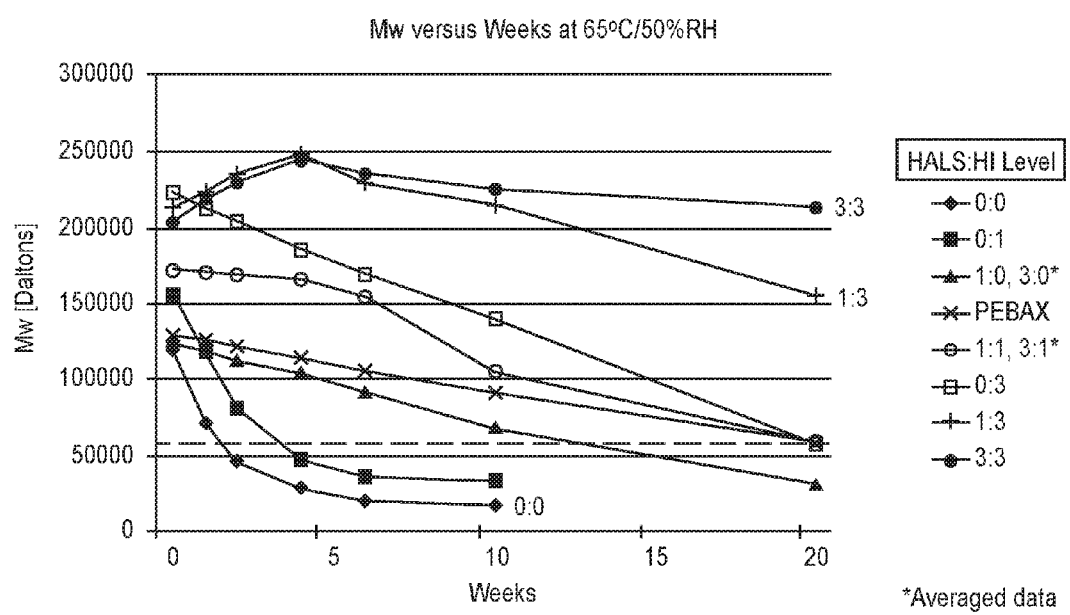
FIG. 1 is a graph of the molecular weight change of an exemplary polymer composition with aging time at 65° C./50% RH.

The present disclosure provides polymer compositions, articles, and methods.

The polymer compositions include additives that provide more hydrolytic stability to a polymer than the polymer without the additives.

In one embodiment, there is provided a composition that includes: a polymer including functional groups having hydrolyzable bonds; a carbodiimide compound; and a weak base; wherein the carbodiimide compound and weak base are used in amounts effective to decrease the rate and/or extent of hydrolytic degradation of the polymer relative to either used alone in the same amount with the polymer.

In one embodiment, there is provided a composition that includes: a polymer including functional groups having hydrolyzable bonds; a carbodiimide compound; and a hindered amine; wherein the carbodiimide compound and hindered amine are used in amounts effective to decrease the rate and/or extent of hydrolytic degradation of the polymer relative to either used alone in the same amount with the polymer.

Such composition (i.e., polymer composition) may be the formulation formed upon initial combination of the components (e.g., polymer, carbodiimide compound, and weak base, or polymer, carbodiimide compound, and hindered amine) prior to being processed (e.g., extruded or otherwise exposed to heat). Alternatively, such composition may be an intermediate formed during processing. Or, such composition may form all or part of a final article (e.g., a medical article).

Polymers

Suitable polymers include functional groups having hydrolyzable bonds. Examples of such functional groups include ester groups, amide groups, imide groups, urethane groups, urea groups, carbonate groups, or combinations thereof.

Polymers having such functional groups include, for example, polyesters such as polyethylene terephthalate, polyamides such as nylon, polybutylene terephthalate, polylactides (PLA), polyglycolides (PLGA), polyimides, polyurethanes, or combinations thereof. In this context, "combinations" refers to mixtures, blends, or copolymers thereof (e.g., polyether block amides, polyester polyurethane).

In certain embodiments, the polymer includes a polyamide, a polyether, a mixture, a blend, or a copolymer thereof. Exemplary such polymers include polyether block amides (PEBA such as that available under the tradename PEBAX from Arkema).

In certain embodiments, the polymers are thermoplastic polymers where the mechanical properties rely heavily on the polymer molecular weight.

In certain embodiments, the polymers have a reasonable shelf life, but the hydrolytic degradation can be accelerated by fillers, other additives, or special use conditions.

Carbodiimide Compounds

A carbodiimide compound (e.g., a methanediimine) includes a functional group consisting of the formula RN=C=NR. Although nitrogen-containing, a carbodiimide is not an amine; however, it may be a weak base.

Suitable carbodiimide compounds can be monomeric, oligomeric, or polymeric.

In certain embodiments, the carbodiimide compound is polymeric. Exemplary polymeric carbodiimide compounds include a 2,6- or 2,4,6-isopropyl substituted aromatic polycarbodiimide having a number average molecular weight of 1,000 grams/mole (g/mol) to 50,000 g/mol.

In certain embodiments, exemplary polymeric carbodiimide compounds are represented by the formula (I):

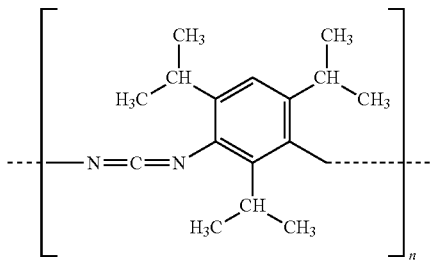

wherein n represents the number of repeat units (e.g., n is from 4 to 250).

In certain embodiments, a carbodiimide compound is sterically hindered. In this context, sterically hindered means there are two alkyl substituents on each of the carbon atoms attached to the nitrogen atoms.

Exemplary sterically hindered carbodiimide compounds are represented by the formula (II):

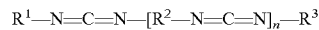

wherein:

n is 0 to 1000 (for certain embodiments, n is 4 to 250);

$R^1$ and $R^3$ individually represent a monovalent aliphatic group having 1 to 40 carbon atoms (for certain embodiments, 1 to 10 carbon atoms), a cycloaliphatic group having 6 to 40 carbon atoms (for certain embodiments, 6 to 20 carbon atoms), an aromatic group having 6 to 40 carbon atoms (for certain embodiments, 6 to 20 carbon atoms), or combinations thereof; and $R^2$ represents a divalent aliphatic group having 1 to 40 carbon atoms (for certain embodiments, 1 to 10 carbon atoms), a cycloaliphatic group having 6 to 40 carbon atoms (for certain embodiments, 6 to 20 carbon atoms), an aromatic group having 6 to 40 carbon atoms (for certain embodiments, 6 to 20 carbon atoms), or combinations thereof.

In certain embodiments of formula (II), one or more of the cycloaliphatic and aromatic groups are substituted with alkyl groups having 1 to 9 carbon atoms. In certain embodiments, the alkyl groups include ethyl, propyl, or isopropyl groups.

In certain embodiments of the compositions of the present disclosure, mixtures of two or more carbodiimide compounds may be used.

Exemplary carbodiimide compounds are disclosed in U.S. Pat. Nos. 5,360,888, 4,987,168, U.S. Pat. Application No. 2007/0066727, and International Publication No. WO 2011/153184.

Commercially available carbodiimide compounds include those available under the trade name STABAXOL (available from Rhein Chemie Corp./Rhein Chemie Additives, a business unit of the specialty chemicals group LANXESS/LANXESS Deutschland GmbH/Cologne, Germany). This includes both monomeric and polymeric compounds, which are disclosed at rheinchemie.com. Other commercially available carbodiimide compounds include those available under the trade names "Stabilizer 7000," "Stabilizer 9000," and "Stabilizer 11,000" (available from Raschig GmbH, Ludwigshafen, Germany).

In certain embodiments, a composition of the present disclosure includes a carbodiimide compound in an amount of at least 0.1 wt-%, at least 0.5 wt-%, or at least 1 wt-%, based on the weight of the polymer alone (i.e., without carbodiimides, weak bases, fillers, or other additives).

In certain embodiments, a composition of the present disclosure includes a carbodiimide compound in an amount of up to 20 wt-%, up to 10 wt-%, or up to 5 wt-%, based on the weight of the polymer alone (i.e., without carbodiimides, weak bases, fillers, or other additives).

Weak Bases and Hindered Amines

Suitable weak bases for use with carbodiimides include organic compounds, inorganic compounds, or combinations thereof. Preferred weak bases are organic compounds (other than the carbodiimide compounds described herein).

Herein, a weak base works with a carbodiimide compound in the presence of a polymer with functional groups having hydrolyzable bonds by a neutralization reaction, without causing base-catalyzed hydrolysis. Although Applicant does not wish to be bound by theory, it is believed that such weak bases work as acid scavengers.

In certain preferred embodiments, the weak base includes an organic compound, in particular an organic amine or imine. The amine and imine compounds include aliphatic, cyclic or hetero cyclic structures (such as pyridine, pyrrole, imidazole, pyrazine, piperidine, pyrimide, pyridazine, quinolone, peperidine, indo etc.). The amine and imine compounds could have more than nitrogen atoms. In addition to organic amine/imine weak bases, other classes of organic weak bases include salt formed from strong base and organic acids.

In certain embodiments, an organic amine may be a monomeric amine, an oligomeric amine, a polymeric amine, or a combination thereof.

In certain embodiments, an organic amine may be a primary amine, a secondary amine, a tertiary amine, or a combination thereof.

In certain embodiments, exemplary tertiary amines may have the following structure: $N(R^4)(R^5)(R^6)$ wherein $R^4$, $R^5$, and $R^6$ individually represent a monovalent aliphatic group having 1 to 1000 carbon atoms, a cycloaliphatic group having 6 to 1000 carbon atoms, an aromatic group having 6 to 1000 carbon atoms, or a combination thereof.

In certain embodiments, exemplary secondary amines may have the following structure: $N(R^4)(R^5)(R^6)$ wherein $R^4$, $R^5$, and $R^6$ individually represent a monovalent aliphatic group having 1 to 1000 carbon atoms, a cycloaliphatic group having 6 to 1000 carbon atoms, an aromatic group having 6 to 1000 carbon atoms, or a combination thereof; and at least one of $R^4$, $R^5$, and $R^6$ is Hydrogen.

In certain embodiments, suitable organic amines may be heterocyclic compounds, such as pyridine, quinolone, pyrrole, indole, pyrimidine, imidazole, and purine.

In certain embodiments, suitable organic amines are (sterically) hindered amines (whether they function as weak bases or not). In this context, "hindered" refers to compounds containing amine groups having two alkyl groups on each of the carbon atoms attached to an amine group.

Exemplary hindered amines include the following (wherein "n" is the number of repeat units in each polymer, and may be the number of repeat units sufficient to create a number average molecular weight of 1000 g/mol to 50,000 g/mol):

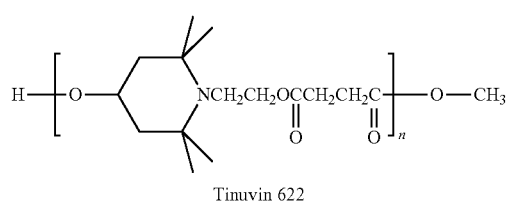

Tinuvin 622

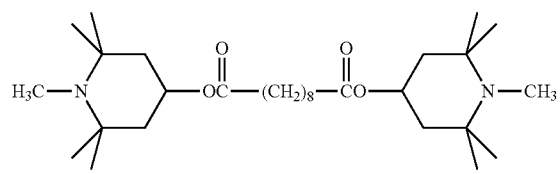

Tinuvin 765

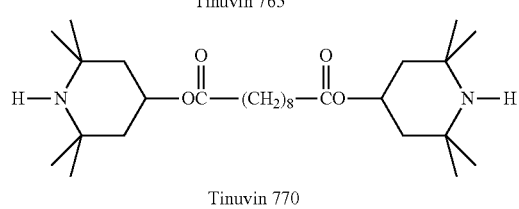

Tinuvin 770

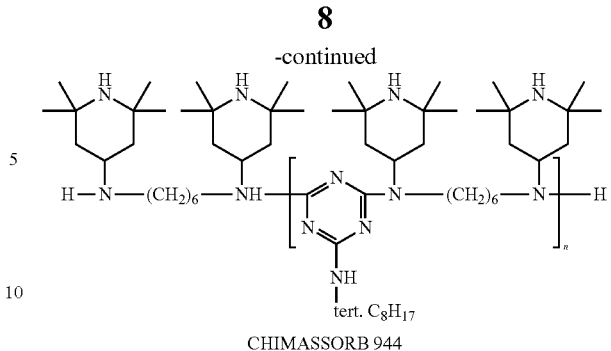

CHIMASSORB 944

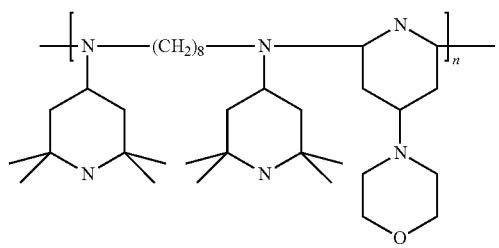

Cyasorb UV3346

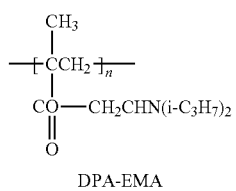

DPA-EMA

Other exemplary hindered amines are disclosed in U.S. Pat. Nos. 9,045,480, 4,520,171, 5,668,198, U.S. Pat. Application No. 2012/0083557, U.S. Pat. Application No. 2005/0004294, and U.S. Pat. Application No. 2008/0033080.

In certain embodiments, hindered amines include one or more groups (formula II), which are incorporated into a hindered amine compound through the R and/or R' groups:

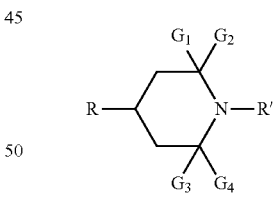

In certain embodiments, hindered amines have the structures (formulas III and IV) (wherein "n" is the number of repeat units in each compound, and may be 1 to 1000):

(III)

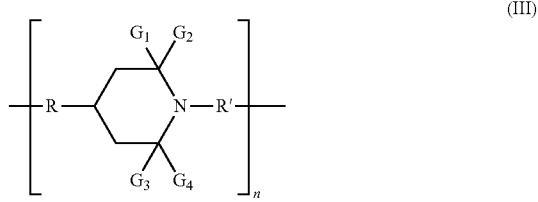

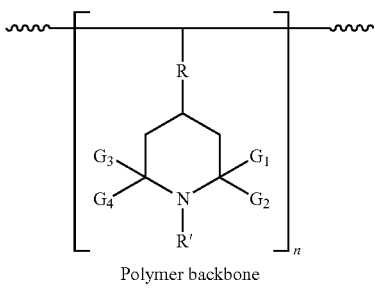

Polymer backbone (IV)

In formulas II-IV:
R' represents hydrogen, oxy, hydroxy, alkyl of 1 to 18 carbon atoms, alkenyl of 3 to 18 carbon atoms, aralkyl of 7 to 9 carbon atoms, cycloalkyl of 5 to 12 carbon atoms, hydroxy alkyl of 2 to 6 carbon atoms, alkoxy alkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms, or bicyclo or nicycloaliphatic oxy radical of 7 to 12 carbon atoms, which may be monovalent or divalent (as shown);

$G_1$, $G_2$, $G_3$, and $G_4$ each independently represents an alkyl group of 1 to 4 carbon atoms, or $G_1$ and $G_2$ and/or $G_3$ and $G_4$ together are pentamethylene; and R represents a divalent organic group.

Commercially available hindered amines include those available under the trade names TINUVIN 123, TINUVIN 144, TINUVIN 622, TINUVIN 765, and TINUVIN 770 (available from BASF SE, Ludwigshafen, Germany) as well as BLS 770 (available from Mayzo Inc., Suwanee, Ga.).

In certain embodiments, an inorganic weak base includes a salt formed between a strong base and a weak acid, a polymeric version thereof, or a combination thereof. Exemplary weak bases include sodium formate, potassium formate, sodium acetate, potassium acetate, sodium propionate, sodium propionate, sodium carbonate, potassium carbonate, calcium carbonate, magnesium carbonate, barium carbonate, hydrogen carbonate, sodium hydrogen carbonate, potassium hydrogen carbonate, calcium hydrogen carbonate, magnesium hydrogen carbonate, barium hydrogen carbonate, or combinations thereof.

In certain embodiments, a weak base includes an inorganic weak base, such as an oxide, a hydroxide, a phosphate, or combinations thereof. Exemplary inorganic weak bases include sodium phosphate, potassium phosphate, calcium hydroxide, calcium oxide, magnesium hydroxide, magnesium oxide, zinc hydroxide, zinc oxide, barium hydroxide, barium oxide, titanium hydroxide, titanium oxide, aluminum hydroxide, aluminum oxide, or combinations thereof.

In certain embodiments, a weak base may also function as a filler. That is, in certain embodiments, a filler (particularly those that are commonly used for radiopacity) could act as a weak base.

In certain embodiments, a weak base is not a filler. That is, in certain embodiments, a filler (particularly those that are commonly used for radiopacity) does not function as a weak base.

In certain embodiments, a composition of the present disclosure includes a weak base in an amount of at least 0.1 wt-%, at least 0.5 wt-%, at least 1 wt-%, at least 2 wt-%, at least 3 wt-%, or at least 4 wt-%, based on the weight of the polymer alone (i.e., without carbodiimides, weak bases, fillers, or other additives).

In certain embodiments, a composition of the present disclosure includes a hindered amine in an amount of at least 0.1 wt-%, at least 0.5 wt-%, at least 1 wt-%, at least 2 wt-%, at least 3 wt-%, or at least 4 wt-%, based on the weight of the polymer alone (i.e., without carbodiimides, other hindered amines, fillers, or other additives).

In certain embodiments, a composition of the present disclosure includes a weak base in an amount of up to 85 wt-%, up to 50 wt-%, up to 25 wt-%, up to 20 wt-%, up to 10 wt-%, or up to 5 wt-%, based on the weight of the polymer alone (i.e., without carbodiimides, weak bases, fillers, or other additives).

In certain embodiments, a composition of the present disclosure includes a hindered amine in an amount of up to 85 wt-%, up to 50 wt-%, up to 25 wt-%, up to 20 wt-%, up to 10 wt-%, or up to 5 wt-%, based on the weight of the polymer alone (i.e., without carbodiimides, hindered amines, fillers, or other additives).

In certain embodiments, a composition of the present disclosure includes a weak base in an amount of at least 0.25% by volume. In certain embodiments, a composition of the present disclosure includes a hindered amine in an amount of at least 0.25% by volume.

In certain embodiments, a composition of the present disclosure includes a weak base in an amount of up to 20% by volume. In certain embodiments, a composition of the present disclosure includes a hindered amine in an amount of up to 20% by volume.

Optional Fillers

In certain embodiments, the polymer includes a filler mixed therein. The filler may be a metal, metal alloy, metal-containing compound, a silica-containing compound, or combinations thereof. In this context, a "metal" refers to transition metals, alkali metals, and alkaline earth metals.

Typical fillers are those commonly used for radiopacity. For example, the filler may be tungsten carbide, barium sulfate, silver, tungsten, tantalum, bismuth, platinum-iridium alloy, bismuth subcarbonate, bismuth trioxide, bismuth oxychloride, glass (such as alum ino-borosilicate), or combinations thereof. In certain embodiments, the filler includes tungsten carbide powder.

Exemplary fillers may be in the form of a powder, spheres, fibers, or particles of irregular shapes. The particle size (i.e., largest dimension of a particle, such as the diameter of a sphere) is typically small enough for a body to dispose of it or degrade it, but typically not nanoparticle size, although the particle size can vary over a wide range.

In certain embodiments, a composition of the present disclosure includes a filler in an amount of greater than 0 volume-%, or at least 5 volume-%, based on the volume of the polymer alone (i.e., without carbodiimides, bases, fillers, or other additives).

In certain embodiments, a composition of the present disclosure includes a filler in an amount of, up to 20 volume-%, or up to 75 volume-%, or up to 95 volume-%, based on the volume of the polymer alone (i.e., without carbodiimides, weak bases, fillers, or other additives).

Optional Additives

In certain embodiments, one or more additives can also be incorporated into compositions of the present disclosure. Such additives may be selected from a light stabilizer, antioxidant, radiopaque agent, echogenetic agent, lubricious agent, colorant, antistatic agent, tackifier, flame retardant, matting agent, or combinations thereof.

In certain embodiments, a composition may include an ultraviolet (UV) light stabilizer, an antioxidant, or a combination thereof.

In certain embodiments, a composition may include a UV light stabilizer. Commercially available UV light stabilizers include those available under the trade names TINUVIN 326, TINUVIN 327, TINUVIN 328, TINUVIN 213, TINUVIN 571, and TINUVIN P.

In certain embodiments, a composition may include an antioxidant. Commercially available antioxidants include those available under the trade names IRGANOX 1010, IRGANOX 245, IRGANOX 1076, IRGANOX 1098, IRGANOX 1135, and IRGANOX 5057.

In certain embodiments, a composition of the present disclosure includes an optional additive in an amount of at least 0.1 wt-%, at least 0.5 wt-%, or at least 1 wt-%, based on the weight of the polymer alone (i.e., without carbodiimides, weak bases, fillers, or other additives).

In certain embodiments, a composition of the present disclosure includes an optional additive in an amount of up to 10 wt-%, or up to 5 wt-%, based on the weight of the polymer alone (i.e., without carbodiim ides, weak bases, fillers, or other additives).

Methods

The present disclosure provides a method for increasing the hydrolytic stability of a polymer that includes functional groups having hydrolyzable bonds. Such functional groups having hydrolyzable bonds include ester groups, amide groups, imide groups, urethane groups, urea groups, carbonate groups, or combinations thereof. In certain embodiments, the polymers particularly susceptible to hydrolysis include a polyamide, polyether, or mixture, blend, or copolymer thereof.

In certain embodiments, a method includes providing said polymer and combining the polymer with a carbodiimide compound and a weak base to form a composition, using standard compounding conditions. In certain embodiments, providing a polymer comprises providing a polymer mixed with a filler. Such fillers are described herein.

In certain embodiments, a method includes providing said polymer and combining the polymer with a carbodiimide compound and a hindered amine to form a composition, using standard compounding conditions. In certain embodiments, providing a polymer comprises providing a polymer mixed with a filler. Such fillers are described herein.

In certain embodiments, the carbodiimide compound and weak base (or hindered amine) are used in amounts effective to decrease the rate and/or extent of hydrolytic degradation of the polymer relative to either used alone in the same amount with the polymer.

In certain embodiments, the decrease in the rate and/or extent of hydrolytic degradation can be determined by measuring properties such as molecular weight, percent elongation, toughness, and/or tensile strength. In certain embodiments, the percent change in one or more of these properties (preferably all of these properties) is less than 30%, or less than 20%, or less than 10% after at least 20 weeks of aging at 65° C./50% RH.

In certain embodiments, the hydrolytic degradation can be reduced or completely stopped to an extent such that there is no measurable difference in one or more properties such as molecular weight, percent elongation, toughness, and/or tensile strength after at least 10 weeks, or after at least 20 weeks, of aging at 65° C./50% RH.

Particularly desirable results occur with the use of a weak base (or hindered amine) in an amount of at least 1, at least 2, at least 3, or at least 4 weight percent, based on the weight of the polymer.

Particularly desirable results occur with the use of a carbodiimide compound in an amount of at least 1, at least 2, at least 3, or at least 4 weight percent, based on the weight of the polymer.

In certain embodiments, particularly desirable results occur with the use of a weak base (or hindered amine) and a carbodiimide compound in amounts of at least 1 weight percent and at least 2 (or at least 3, or at least 4) weight percent, respectively, based on the weight of the polymer.

In certain embodiments, particularly desirable results occur with the use of a weak base (or hindered amine) and a carbodiimide compound in amounts of at least 2 weight percent and at least 2 (or at least 3, or at least 4) weight percent, respectively, based on the weight of the polymer.

In certain embodiments, particularly desirable results occur with the use of a weak base (or hindered amine) and a carbodiimide compound in amounts of at least 3 weight percent and at least 2 (or at least 3, or at least 4) weight percent, respectively, based on the weight of the polymer.

In certain embodiments, particularly desirable results occur with the use of a weak base (or hindered amine) and a carbodiimide compound in amounts of at least 4 weight percent and at least 2 (or at least 3, or at least 4) weight percent, respectively, based on the weight of the polymer.

In certain embodiments, a weak base (or hindered amine) can be used in an amount of up to 20 weight percent, or up to 10 weight percent, based on the weight of the polymer.

In certain embodiments, a carbodiimide compound can be used in an amount of up to 20 weight percent, or up to 10 weight percent, based on the weight of the polymer.

Articles

In certain embodiments, hydrolytically stable polymer compositions described herein are suitable for use in a variety of articles susceptible to hydrolytic degradation, such as medical devices, outerwear, furniture, marine and sporting equipment and sportswear, as well as automotive, aerospace, architectural materials.

The hydrolytically stable polymer compositions described herein are particularly suitable for use in at least a portion of a medical device.

A medical device includes any instrument, apparatus, implement, machine, appliance, implant, in vitro reagent or calibrator, material or other similar or related article, intended by the manufacturer to be used, alone or in combination, for mammals (e.g., human beings) for one or more of the specific purpose(s) of: diagnosis, prevention, monitoring, treatment, or alleviation of disease; diagnosis, monitoring, treatment, or alleviation of or compensation for an injury; investigation, replacement, modification, or support of the anatomy or of a physiological process; supporting or sustaining life; control of conception; disinfection of medical devices; providing information for medical purposes by means of in vitro examination of specimens derived from the subject, and which does not achieve its primary intended action in or on the subject by pharmacological, immunological or metabolic means, but which may be assisted in its function by such means.

Figure 4:
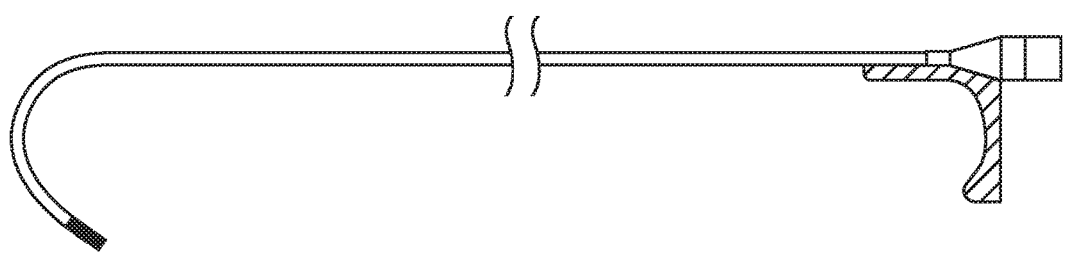
FIG. 4 is a perspective view of one embodiment of a medical article of the present disclosure.

Specific examples of medical devices include a catheter component such as a catheter tip, catheter shaft, catheter markers, device markers, or any radiopaque markers. FIG. 4 shows a catheter with a tip (shown as shaded) that includes a polymeric composition as described herein.

EXEMPLARY EMBODIMENTS

Embodiment 1 is a composition comprising: a polymer comprising functional groups having hydrolyzable bonds; a carbodiimide compound; and a weak base other than the carbodiimide compound; wherein the carbodiimide compound and weak base other than the carbodiimide compound are used in amounts effective to decrease the rate and/or extent of hydrolytic degradation of the polymer relative to either used alone in the same amount with the polymer.

Embodiment 2 is the composition of embodiment 1 wherein the weak base comprises an organic compound, an inorganic compound, or a combination thereof.

Embodiment 3 is the composition of embodiment 2 wherein the weak base comprises an organic compound.

Embodiment 4 is the composition of embodiment 3 wherein the weak base comprises an organic amine.

Embodiment 5 is the composition of embodiment 4 wherein the organic amine weak base comprises a monomeric amine, an oligomeric amine, a polymeric amine, or a combination thereof.

Embodiment 6 is the composition of embodiment 4 or 5 wherein the organic amine weak base comprises a primary amine, a secondary amine, a tertiary amine, or a combination thereof.

Embodiment 7 is the composition of any one of embodiments 4 through 6 wherein the organic amine weak base comprises a hindered amine.

Embodiment 8 is the composition of embodiment 7 wherein the hindered amine weak base comprises:

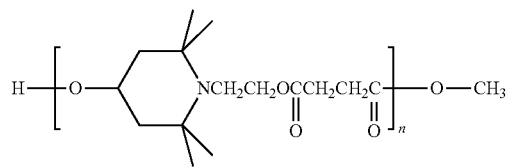

Tinuvin 622

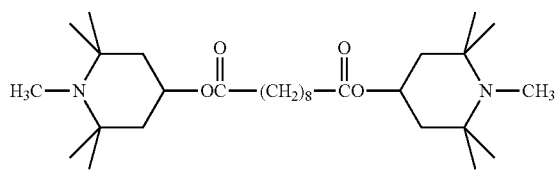

Tinuvin 765

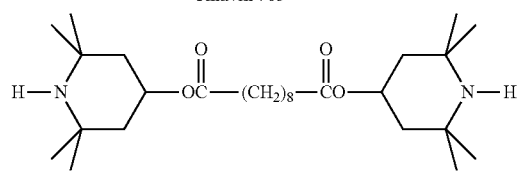

Tinuvin 770

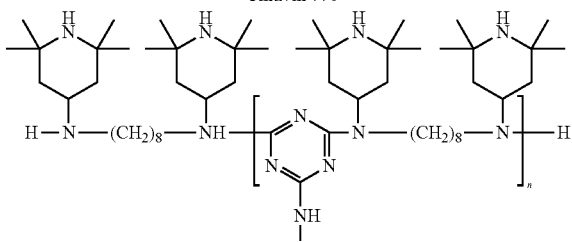

CHIMASSORB 944

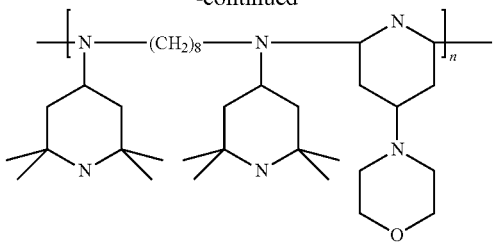

Cyasorb UV3346

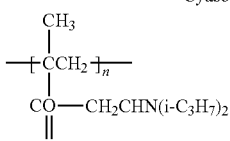

DPA-EMA wherein n represents a number of repeat units in each polymer.

Embodiment 9 is the composition of embodiment 8 wherein n is the number of repeat units sufficient to create a number average molecular weight of 1000 g/mol to 50,000 g/mol.

Embodiment 10 is the composition of embodiment 2 wherein the weak base comprises a salt formed between a strong base and a weak acid, a polymeric version thereof, or a combination thereof.

Embodiment 11 is the composition of embodiment 10 wherein the weak base comprises sodium formate, potassium formate, sodium acetate, potassium acetate, sodium propionate, sodium propionate, sodium carbonate, potassium carbonate, calcium carbonate, magnesium carbonate, barium carbonate, hydrogen carbonate, sodium hydrogen carbonate, potassium hydrogen carbonate, calcium hydrogen carbonate, magnesium hydrogen carbonate, barium hydrogen carbonate, or combinations thereof.

Embodiment 12 is the composition of embodiment 2 wherein the weak base comprises an inorganic weak base.

Embodiment 13 is the composition of embodiment 12 wherein the inorganic weak base comprises an oxide, a hydroxide, a phosphate, or combinations thereof.

Embodiment 14 is the composition of embodiment 13 wherein the inorganic weak base comprises sodium phosphate, potassium phosphate, calcium hydroxide, calcium oxide, magnesium hydroxide, magnesium oxide, zinc hydroxide, zinc oxide, barium hydroxide, barium oxide, titanium hydroxide, titanium oxide, aluminum hydroxide, aluminum oxide, or combinations thereof.

Embodiment 15 is the composition of any one of embodiments 1 through 14 wherein the weak base is present in an amount of at least 0.1 wt-%, based on the weight of the polymer.

Embodiment 16 is the composition of embodiment 15 wherein the weak base is present in an amount of at least 1 wt-%, based on the weight of the polymer.

Embodiment 17 is the composition of any one of embodiments 1 through 16 wherein the weak base is present in an amount of up to 85 wt-%, based on the weight of the polymer.

Embodiment 18 is the composition of embodiment 17 wherein the weak base is present in an amount of up to 5 wt-%, based on the weight of the polymer.

Embodiment 19 is the composition of any one of embodiments 1 through 18 wherein the weak base is present in an amount of at least 0.25% by volume.

Embodiment 20 is the composition of any one of embodiments 1 through 19 wherein the weak base is present in an amount of up to 20% by volume.

Embodiment 21 is a composition comprising: a polymer comprising functional groups having hydrolyzable bonds; a carbodiimide compound; and a hindered amine; wherein the carbodiimide compound and hindered amine are used in amounts effective to decrease the rate and/or extent of hydrolytic degradation of the polymer relative to either used alone in the same amount with the polymer.

Embodiment 22 is the composition of embodiment 21 wherein the hindered amine comprises one or more compounds of the formulas (III) and (IV):

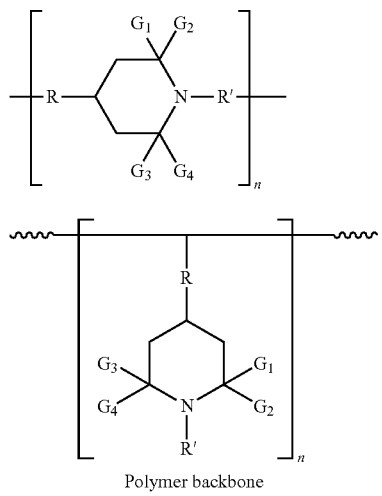

(III)

(IV)

Polymer backbone wherein:
R' represents hydrogen, oxy, hydroxy, alkyl of 1 to 18 carbon atoms, alkenyl of 3 to 18 carbon atoms, aralkyl of 7 to 9 carbon atoms, cycloalkyl of 5 to 12 carbon atoms, hydroxy alkyl of 2 to 6 carbon atoms, alkoxy alkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms, or bicyclo or nicycloaliphatic oxy radical of 7 to 12 carbon atoms;
G1, G2, G3, and G4 each independently represents an alkyl group of 1 to 4 carbon atoms, or G1 and G2 and/or G3 and G4 together are pentamethylene;
R represents a divalent organic group; and
n represents a number of repeat units (e.g., 1 to 1000).

Embodiment 23 is the composition of embodiment 21 or 22 wherein the hindered amine comprises:

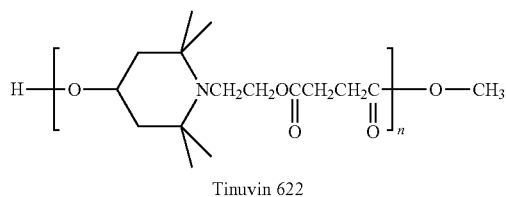

Tinuvin 622

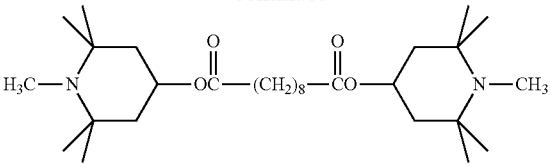

Tinuvin 765

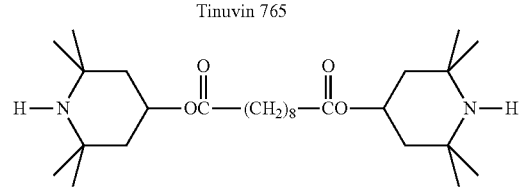

Tinuvin 770

Embodiment 24 is the composition of any one of embodiments 21 through 23 wherein the hindered amine is present in an amount of at least 0.1 wt-%, based on the weight of the polymer.

Embodiment 25 is the composition of embodiment 24 wherein the hindered amine is present in an amount of at least 1 wt-%, based on the weight of the polymer.

Embodiment 26 is the composition of any one of embodiments 21 through 25 wherein the hindered amine is present in an amount of up to 85 wt-%, based on the weight of the polymer.

Embodiment 27 is the composition of embodiment 26 wherein the hindered amine is present in an amount of up to 5 wt-%, based on the weight of the polymer.

Embodiment 28 is the composition of any one of embodiments 21 through 27 wherein the hindered amine is present in an amount of at least 0.25% by volume.

Embodiment 29 is the composition of any one of embodiments 21 through 28 wherein the hindered amine is present in an amount of up to 20% by volume.

Embodiment 30 is the composition of any one of embodiments 1 through 29 which forms all or part of a final article.

Embodiment 31 is the composition of embodiment 30 wherein the final article is a medical device.

Embodiment 32 is the composition of any one of embodiments 1 through 31 further comprising a filler.

Embodiment 33 is the composition of embodiment 32 wherein the filler comprises powder, spheres, fibers, or particles of irregular shapes.

Embodiment 34 is the composition of embodiment 32 or 33 wherein the filler comprises a metal, metal alloy, metal-containing compound, a silica-containing compound, or combinations thereof.

Embodiment 35 is the composition of any one of embodiments 32 through 34 wherein the filler comprises tungsten carbide, barium sulfate, silver, tungsten, tantalum, bismuth, platinum-iridium alloy, bismuth subcarbonate, bismuth trioxide, bismuth oxychloride, glass, or combinations thereof.

Embodiment 36 is the composition of embodiment 35 wherein the filler comprises tungsten carbide powder.

Embodiment 37 is the composition of any one of embodiments 1 through 36 wherein the functional groups of the polymer comprise ester groups, amide groups, imide groups, urethane groups, urea groups, carbonate groups, or combinations thereof.

Embodiment 38 is the composition of embodiment 37 wherein the polymer comprises a polyamide, polyether, or combinations thereof.

Embodiment 39 is the composition of any one of embodiments 1 through 38 wherein the carbodiimide compound is monomeric or oligomeric.

Embodiment 40 is the composition of any one of embodiments 1 through 38 wherein the carbodiimide compound is polymeric.

Embodiment 41 is the composition of embodiment 40 wherein the polymeric carbodiimide compound comprises a 2,6- or 2,4,6-isopropyl substituted aromatic polycarbodiimide having a number average molecular weight of 1,000 g/mol to 50,000 g/mol.

Embodiment 42 is the composition of embodiment 41 wherein the polymeric carbodiimide compound is represented by the formula (I):

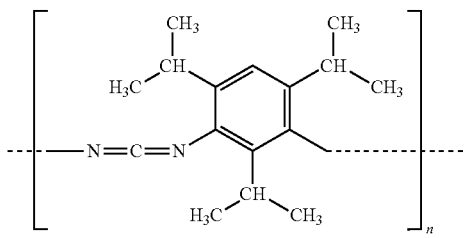

wherein n represents a number of repeat units.

Embodiment 43 is the composition of embodiment 42 wherein n is from 4 to 250 in formula (I).

Embodiment 44 is the composition of any one of embodiments 1 through 43 wherein the carbodiimide compound comprises a sterically hindered carbodiimide represented by the formula (II):

$$R^1-N=C=N-[R^2-N=C=N]_n-R^3$$

wherein:
n is 0 to 1000;
$R^1$ and $R^3$ individually represent a monovalent aliphatic group having 1 to 40 carbon atoms, a cycloaliphatic group having 6 to 40 carbon atoms, an aromatic group having 6 to 40 carbon atoms, or combinations thereof; and
$R^2$ represents a divalent aliphatic group having 1 to 40 carbon atoms, a cycloaliphatic group having 6 to 40 carbon atoms, an aromatic group having 6 to 40 carbon atoms, or combinations thereof.

Embodiment 45 is the composition of embodiment 44 wherein n is 4 to 25 in formula (II).

Embodiment 46 is the composition of embodiment 44 or 45 wherein $R^1$ and $R^3$ in formula (II) individually represent a monovalent aliphatic group having 1 to 10 carbon atoms, a cycloaliphatic group having 6 to 20 carbon atoms, an aromatic group having 6 to 20 carbon atoms, or combinations thereof.

Embodiment 47 is the composition of any one of embodiments 44 through 46 wherein one or more of the cycloaliphatic and aromatic groups in formula (II) are substituted with alkyl groups having 1 to 9 carbon atoms.

Embodiment 48 is the composition of embodiment 47 wherein the alkyl groups comprise ethyl, propyl, or isopropyl groups.

Embodiment 49 is the composition of any one of embodiments 1 through 48 wherein the carbodiimide compound comprises a mixture of carbodiimide compounds.

Embodiment 50 is the composition of any one of embodiments 1 through 49 further comprising one or more additives selected from a light stabilizer, antioxidant, radiopaque agent, echogenetic agent, lubricious agent, colorant, antistatic agent, tackifier, flame retardant, matting agent, and combinations thereof.

Embodiment 51 is the composition of embodiment 50 wherein the one or more additives is selected from a UV light stabilizer, an antioxidant, and a combination thereof.

Embodiment 52 is the composition of embodiment 51 wherein the one or more additives is selected from a UV light stabilizer.

Embodiment 53 is the composition of embodiment 51 or 52 wherein the one or more additives is selected from an antioxidant.

Embodiment 54 is the composition of any one of embodiments 1 through 53 wherein the carbodiimide compound is present in an amount of at least 0.1 wt-%, based on the weight of the polymer.

Embodiment 55 is the composition of embodiment 54 wherein the carbodiimide compound is present in an amount of at least 1 wt-%, based on the weight of the polymer.

Embodiment 56 is the composition of any one of embodiments 1 through 55 wherein the carbodiimide compound is present in an amount of up to 20 wt-%, based on the weight of the polymer.

Embodiment 57 is the composition of embodiment 56 wherein the carbodiimide compound is present in an amount of up to 5 wt-%, based on the weight of the polymer.

Embodiment 58 is an article comprising the composition of any one of embodiments 1 through 57.

Embodiment 59 is the article of embodiment 58 which is a medical device.

Embodiment 60 is the article of embodiment 59 wherein the composition forms a catheter component.

Embodiment 61 is a method for increasing the hydrolytic stability of a polymer comprising functional groups having hydrolyzable bonds, the method comprising:
providing a polymer comprising functional groups having hydrolyzable bonds; and
combining the polymer with a carbodiimide compound and a weak base other than the carbodiimide compound to form a composition;
wherein the carbodiimide compound and weak base other than the carbodiimide compound are used in amounts effective to decrease the rate and/or extent of hydrolytic degradation of the polymer relative to either used alone in the same amount with the polymer.

Embodiment 62 is the method of embodiment 61 wherein the weak base comprises an organic compound, an inorganic compound, or a combination thereof.

Embodiment 63 is the method of embodiment 62 wherein the weak base comprises an organic compound.

Embodiment 64 is the method of embodiment 63 wherein the organic compound comprises an organic amine.

Embodiment 65 is the method of embodiment 64 wherein the organic amine weak base comprises a monomeric amine, an oligomeric amine, a polymeric amine, or a combination thereof.

Embodiment 66 is the method of embodiment 64 or 65 wherein the organic amine weak base comprises a primary amine, a secondary amine, a tertiary amine, or a combination thereof.

Embodiment 67 is the method of any one of embodiments 64 through 66 wherein the organic amine weak base comprises a hindered amine.

Embodiment 68 is the method of embodiment 67 wherein the hindered amine weak base comprises:

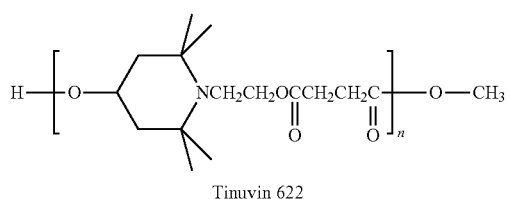

Tinuvin 622

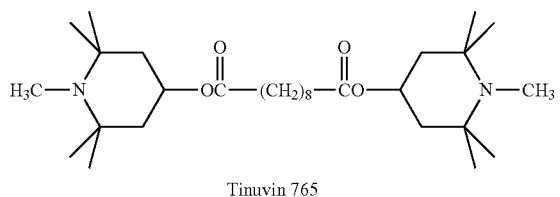

Tinuvin 765

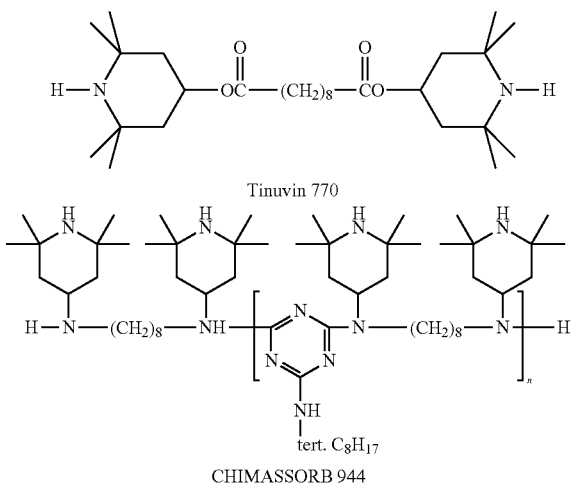

Tinuvin 770

CHIMASSORB 944

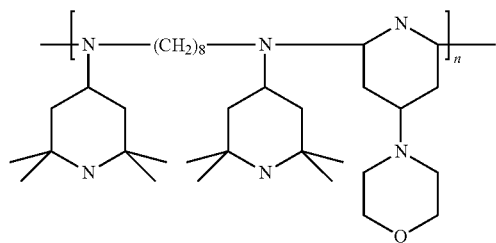

Cyasorb UV3346

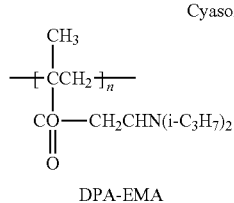

DPA-EMA wherein n represents a number of repeat units in each polymer.

Embodiment 69 is the method of embodiment 68 wherein n is the number of repeat units sufficient to create a number average molecular weight of 1000 g/mol to 50,000 g/mol.

Embodiment 70 is the method of embodiment 62 wherein the weak base comprises a salt formed between a strong base and a weak acid, a polymeric version thereof, or a combination thereof.

Embodiment 71 is the method of embodiment 70 wherein the weak base comprises sodium formate, potassium formate, sodium acetate, potassium acetate, sodium propionate, sodium propionate, sodium carbonate, potassium carbonate, calcium carbonate, magnesium carbonate, barium carbonate, hydrogen carbonate, sodium hydrogen carbonate, potassium hydrogen carbonate, calcium hydrogen carbonate, magnesium hydrogen carbonate, barium hydrogen carbonate, or combinations thereof.

Embodiment 72 is the method of embodiment 62 wherein the weak base comprises an inorganic weak base.

Embodiment 73 is the method of embodiment 72 wherein the inorganic weak base comprises an oxide, a hydroxide, a phosphate, or combinations thereof.

Embodiment 74 is the method of embodiment 73 wherein the inorganic weak base comprises sodium phosphate, potassium phosphate, calcium hydroxide, calcium oxide, magnesium hydroxide, magnesium oxide, zinc hydroxide, zinc oxide, barium hydroxide, barium oxide, titanium hydroxide, titanium oxide, aluminum hydroxide, aluminum oxide, or combinations thereof.

Embodiment 75 is the method of any one of embodiments 61 through 74 wherein the weak base is present in an amount of at least 0.1 wt-%, based on the weight of the polymer.

Embodiment 76 is the method of embodiment 75 wherein the weak base is present in an amount of at least 1 wt-%, based on the weight of the polymer.

Embodiment 77 is the method of any one of embodiments 61 through 76 wherein the weak base is present in an amount of up to 85 wt-%, based on the weight of the polymer.

Embodiment 78 is the method of embodiment 77 wherein the weak base is present in an amount of up to 5 wt-%, based on the weight of the polymer.

Embodiment 79 is the method of any one of embodiments 61 through 78 wherein the weak base is present in an amount of at least 0.25% by volume.

Embodiment 80 is the method of any one of embodiments 61 through 79 wherein the weak base is present in an amount of up to 20% by volume.

Embodiment 81 is a method for increasing the hydrolytic stability of a polymer comprising functional groups having hydrolyzable bonds, the method comprising:

providing a polymer comprising functional groups having hydrolyzable bonds; and combining the polymer with a carbodiimide compound and a hindered amine to form a composition;

wherein the carbodiimide compound and hindered amine are used in amounts effective to decrease the rate and/or extent of hydrolytic degradation of the polymer relative to either used alone in the same amount with the polymer.

Embodiment 82 is the method of embodiment 81 wherein the hindered amine comprises one or more compounds of the formulas (III) and (IV):

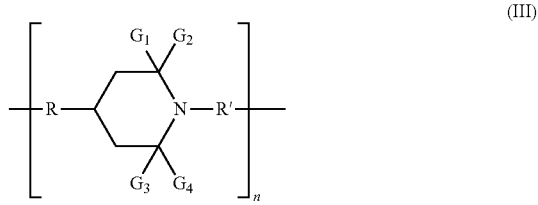

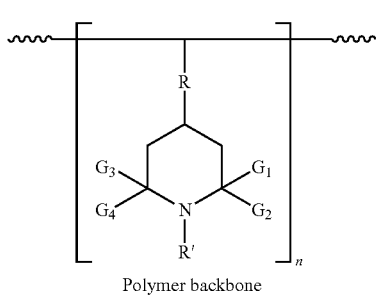

Polymer backbone wherein:
R' represents hydrogen, oxy, hydroxy, alkyl of 1 to 18 carbon atoms, alkenyl of 3 to 18 carbon atoms, aralkyl of 7 to 9 carbon atoms, cycloalkyl of 5 to 12 carbon atoms, hydroxy alkyl of 2 to 6 carbon atoms, alkoxy alkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms, or bicyclo or nicycloaliphatic oxy radical of 7 to 12 carbon atoms;

G1, G2, G3, and G4 each independently represents an alkyl group of 1 to 4 carbon atoms, or G1 and G2 and/or G3 and G4 together are pentamethylene;

R represents a divalent organic group; and n represents a number of repeat units (e.g., 1 to 1000).

Embodiment 83 is the method of embodiment 81 or 82 wherein the hindered amine comprises:

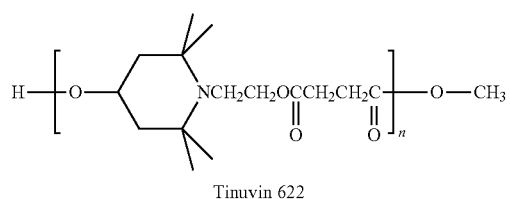

Tinuvin 622

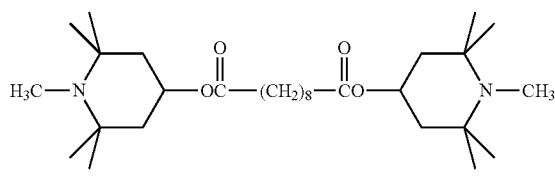

Tinuvin 765

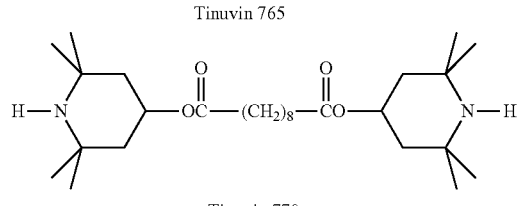

Tinuvin 770

Embodiment 84 is the method of any one of embodiments 81 through 83 wherein the hindered amine is present in an amount of at least 0.1 wt-%, based on the weight of the polymer.

Embodiment 85 is the method of embodiment 84 wherein the hindered amine is present in an amount of at least 1 wt-%, based on the weight of the polymer.

Embodiment 86 is the method of any one of embodiments 81 through 85 wherein the hindered amine is present in an amount of up to 85 wt-%, based on the weight of the polymer.

Embodiment 87 is the method of embodiment 86 wherein the hindered amine is present in an amount of up to 5 wt-%, based on the weight of the polymer.

Embodiment 88 is the method of any one of embodiments 81 through 87 wherein the hindered amine is present in an amount of at least 0.25% by volume.

Embodiment 89 is the method of any one of embodiments 81 through 88 wherein the hindered amine is present in an amount of up to 20% by volume.

Embodiment 90 is the method of any one of embodiments 61 through 89 wherein the composition forms all or part of a final article.

Embodiment 91 is the method of embodiment 90 wherein the final article is a medical device.

Embodiment 92 is the method of any one of embodiments 61 through 91 wherein providing a polymer comprises providing a polymer mixed with a filler.

Embodiment 93 is the method of embodiment 92 wherein the filler comprises powder, spheres, fibers, or particles of irregular shapes.

Embodiment 94 is the method of embodiment 92 or 93 wherein the filler comprises a metal, metal alloy, metal-containing compound, a silica-containing compound, or combinations thereof.

Embodiment 95 is the method of any one of embodiments 92 through 94 wherein the filler comprises tungsten carbide, barium sulfate, silver, tungsten, tantalum, bismuth, platinum-iridium alloy, bismuth subcarbonate, bismuth trioxide, bismuth oxychloride, glass, or combinations thereof.

Embodiment 96 is the method of embodiment 95 wherein the filler comprises tungsten carbide powder.

Embodiment 97 is the method of any one of embodiments 61 through 96 wherein the functional groups of the polymer comprise ester groups, amide groups, imide groups, urethane groups, urea groups, carbonate groups, or combinations thereof.

Embodiment 98 is the method of embodiment 97 wherein the polymer comprises a polyamide, polyether, or combinations thereof.

Embodiment 99 is the method of any one of embodiments 61 through 98 wherein the carbodiimide compound is monomeric or oligomeric.

Embodiment 100 is the method of any one of embodiments 61 through 98 wherein the carbodiimide compound is polymeric.

Embodiment 101 is the method of embodiment 100 wherein the polymeric carbodiimide compound comprises a 2,6- or 2,4,6-isopropyl substituted aromatic polycarbodiimide having a number average molecular weight of 1,000 g/mol to 50,000 g/mol.

Embodiment 102 is the method of embodiment 101 wherein the polymeric carbodiimide compound is represented by the formula (I):

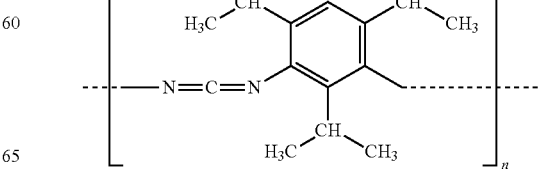

wherein n represents a number of repeat units.

Embodiment 103 is the method of embodiment 102 wherein n is from 4 to 250 in formula (I).

Embodiment 104 is the method of any one of embodiments 61 through 103 wherein the carbodiimide compound comprises a sterically hindered carbodiimide represented by the formula (II):

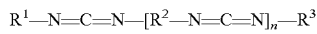

wherein:
n is 0 to 1000;
$R^1$ and $R^3$ individually represent a monovalent aliphatic group having 1 to 40 carbon atoms, a cycloaliphatic group having 6 to 40 carbon atoms, an aromatic group having 6 to 40 carbon atoms, or combinations thereof; and
$R^2$ represents a divalent aliphatic group having 1 to 40 carbon atoms, a cycloaliphatic group having 6 to 40 carbon atoms, an aromatic group having 6 to 40 carbon atoms, or combinations thereof.

Embodiment 105 is the method of embodiment 104 wherein n is 4 to 25 in formula (II).

Embodiment 106 is the method of embodiment 104 or 105 wherein $R^1$ and $R^3$ in formula (II) individually represent a monovalent aliphatic group having 1 to 10 carbon atoms, a cycloaliphatic group having 6 to 20 carbon atoms, an aromatic group having 6 to 20 carbon atoms, or combinations thereof.

Embodiment 107 is the method of any one of embodiments 104 through 106 wherein one or more of the cycloaliphatic and aromatic groups in formula (II) are substituted with alkyl groups having 1 to 9 carbon atoms.

Embodiment 108 is the method of embodiment 107 wherein the alkyl groups comprise ethyl, propyl, or isopropyl groups.

Embodiment 109 is the method of any one of embodiments 61 through 108 wherein providing a carbodiimide compound comprises providing a mixture of carbodiimide compounds.

Embodiment 110 is the method of any one of embodiments 61 through 109 wherein combining the polymer with a carbodiimide compound and a hindered amine to form a composition further comprises combining the polymer with one or more additives selected from a light stabilizer, antioxidant, radiopaque agent, echogenetic agent, lubricious agent, colorant, antistatic agent, tackifier, flame retardant, matting agent, and combinations thereof.

Embodiment 111 is the method of embodiment 110 wherein the one or more additives is selected from a UV light stabilizer, an antioxidant, or a combination thereof.

Embodiment 112 is the method of embodiment 111 wherein the one or more additives is selected from a UV light stabilizer.

Embodiment 113 is the method of embodiment 111 or 112 wherein the one or more additives is selected from an antioxidant.

Embodiment 114 is the method of any one of embodiments 61 through 113 wherein the carbodiimide compound is present in an amount of at least 0.1 wt-%, based on the weight of the polymer.

Embodiment 115 is the method of embodiment 114 wherein the carbodiimide compound is present in an amount of at least 1 wt-%, based on the weight of the polymer.

Embodiment 116 is the method of any one of embodiments 61 through 115 wherein the carbodiimide compound is present in an amount of up to 20 wt-%, based on the weight of the polymer.

Embodiment 117 is the method of embodiment 116 wherein the carbodiimide compound is present in an amount of up to 5 wt-%, based on the weight of the polymer.

Embodiment 118 is the composition, method, or article of any one of embodiments 1 through 117 wherein the decrease in the rate and/or extent of hydrolytic degradation is determined by measuring molecular weight, percent elongation, toughness, and/or tensile strength.

Embodiment 119 is the composition, method, or article of embodiment 118 wherein the percent change in one or more of molecular weight, percent elongation, toughness, and/or tensile strength (preferably all of these properties) is less than 30%, or less than 20%, or less than 10% after at least 20 weeks of aging at 65° C./50% RH.

Embodiment 120 is the composition, method, or article of embodiment 119 wherein the hydrolytic degradation can be reduced or completely stopped to an extent such that there is no measurable difference in one or more properties such as molecular weight, percent elongation, toughness, and/or tensile strength after at least 10 weeks, or after at least 20 weeks, of aging at 65° C./50% RH.

Embodiment 121 is the composition, method, or article of any one of embodiments 1 to 120 wherein the weak base (or hindered amine) is used in an amount of at least 1, at least 2, at least 3, or at least 4 weight percent, based on the weight of the polymer.

Embodiment 122 is the composition, method, or article of any one of embodiments 1 to 121 wherein the carbodiimide compound is used in an amount of at least 1, at least 2, at least 3, or at least 4 weight percent, based on the weight of the polymer.

Embodiment 123 is the composition, method, or article of embodiment 122 wherein the weak base (or hindered amine) and the carbodiimide compound are used in amounts of at least 1 weight percent and at least 2 (or at least 3 or at least 4) weight percent, respectively, based on the weight of the polymer.

Embodiment 124 is the composition, method, or article of embodiment 123 wherein the weak base (or hindered amine) and the carbodiimide compound are used in amounts of at least 2 weight percent and at least 2 (or at least 3 or at least 4) weight percent, respectively, based on the weight of the polymer.

Embodiment 125 is the composition, method, or article of embodiment 124 wherein the weak base (or hindered amine) and the carbodiimide compound are used in amounts of at least 3 weight percent and at least 2 (or at least 3 or at least 4) weight percent, respectively, based on the weight of the polymer.

Embodiment 126 is the composition, method, or article of embodiment 125 wherein the weak base (or hindered amine) and the carbodiimide compound are used in amounts of at least 4 weight percent and at least 2 (or at least 3 or at least 4) weight percent, respectively, based on the weight of the polymer.

EXAMPLES

Objects and advantages of this disclosure are further illustrated by the following examples, but the particular materials and amounts thereof recited in these examples, as well as other conditions and details, should not be construed to unduly limit this disclosure.

Example 1: Mixing

Polyether-block-amide (PEBA) resin (Type: PEBAX 3533) was purchased from Arkema, Inc. The PEBAX resin was dried in a desiccant drier until the moisture content was less than 0.01% by weight. Tungsten carbide powder (WC), an antioxidant (AO) (IRGANOX 1010), a UV absorber (UVA) (TINUVIN 326), a hindered amine light stabilizer (HALS) (TINUVIN 622, CAS 65447-77-0), and a carbodi-imide hydrolysis inhibitor (HI) (Stabilizer 9000, CAS 29963-44-8 and 29117-01-9) were added to the formulations based on Table 1. The AO and UVA were used at approximately 1% by weight of the PEBAX resin in all compounded formulations.

The HALS and HI were evaluated at various loading levels. Fifty pounds of each formulation was made by multiplying the amounts in Table 1 by 0.5. The additives were pre-mixed and added to the PEBAX resin to homogenize prior to compounding. The sample of neat PEBAX resin did not go through the mixing and compounding process.

Example 3: Compression Molding Slabs

Compounded pellets and PEBAX resin were vacuum dried at 60° C. for a minimum of 12 hours, and compression molded into slabs, using an 0.025 inch thick by 5 inches×5 inches frame, at 238° C. using a standard compression molding procedure.

Example 4: Humidity Aging and Evaluation Methods

The compounded pellets, PEBAX resin pellets, and the compression molded sheets were aged in an environmental chamber at 65° C. and humidity of 50% relative humidity (RH). The samples were evaluated at weeks 1, 2, 4, 6, 10, and 20. The molecular weight was determined on the pellets using gel permeation chromatography (GPC). The tensile

TABLE 1

Formulations

| Formulation Descriptions | | | Formulation Components | | | | |
|---|---|---|---|---|---|---|---|
| HALS:HI Level | CODES: 0 = none 1 = low level 3 = high level W = WC HALS:HI:UVA:AO | Pebax Additives | Hindered amine light stabilizer (HALS) Tinuvin 622 | Hydrolysis inhibitor (HI) Stabilizer 9000 | UV absorber (UVA) Tinuvin 326 | Antioxidant (AO) Irganox 1010 | Tungsten carbide (WC) |
| 0:0 | 0011W | 3 | 0 | 0 | 0.249 | 0.249 | 74.399 |
| 1:0 | 1011W | 4 | 0.327 | 0 | 0.272 | 0.272 | 73.110 |
| 3:0 | 3011W | 4 | 0.750 | 0 | 0.250 | 0.250 | 74.200 |
| 0:1 | 0111W | 4 | 0 | 0.250 | 0.250 | 0.250 | 74.200 |
| 0:3 | 0311W | 4 | 0 | 0.796 | 0.249 | 0.249 | 73.794 |
| 1:1 | 1111W | 5 | 0.251 | 0.251 | 0.251 | 0.251 | 74.196 |
| 1:3 | 1311W | 5 | 0.251 | 0.800 | 0.251 | 0.251 | 74.196 |
| 3:1 | 3111W | 5 | 0.800 | 0.251 | 0.251 | 0.251 | 74.196 |
| 3:3 | 3311W | 5 | 0.800 | 0.800 | 0.250 | 0.250 | 74.200 |
| n/a | n/a | 0 | 0 | 0 | 0 | 0 | 0 |

| | Formulation Components | | | | | |
|---|---|---|---|---|---|---|
| HALS:HI Level | Pebax 3533 | SUM | HALS | HI | UVA | AO |
| | | | Wt % to Pebax | | | |
| 0:0 | 25.104 | 100 | 0% | 0% | 0.99% | 0.99% |
| 1:0 | 26.019 | 100 | 1.26% | 0% | 1.05% | 1.05% |
| 3:0 | 24.550 | 100 | 3.05% | 0% | 1.02% | 1.02% |
| 0:1 | 25.050 | 100 | 0% | 1.00% | 1.00% | 1.00% |
| 0:3 | 24.913 | 100 | 0% | 3.19% | 1.00% | 1.00% |
| 1:1 | 24.799 | 100 | 1.01% | 1.01% | 1.01% | 1.01% |
| 1:3 | 24.250 | 100 | 1.04% | 3.30% | 1.04% | 1.04% |
| 3:1 | 24.250 | 100 | 3.30% | 1.04% | 1.04% | 1.04% |
| 3:3 | 23.700 | 100 | 3.38% | 3.38% | 1.05% | 1.05% |
| n/a | 0 | 0 | 0 | 0 | 0 | 0 |

Example 2: Compounding

The mixture for each compounded formulation was fed through a hopper into a twin screw extruder under a dry nitrogen blanket. The hot extrudate was cooled in a water bath, vacuum dried to remove surface moisture, and fed into a pelletizer. The pellets from each formulation group were dried in a desiccant dryer at 200° F./93° C. and −40° F. dew point until the moisture content was <0.01% by weight. After each formulation was dried, the pellets were transferred to a foil bag that was vacuum evacuated and heat sealed.

properties of dog bone samples (ASTM die D638_14 type V) were evaluated based on ASTM D638-08, using an INSTRON test system, a gauge length (extensometer) of 0.375 inch, a jaw separation of 1 inch, and a crosshead speed of 5 inches per minute.

Example 5: Chemistry of Hydrolysis Inhibitors

"Stabilizer 9000" (available from Raschig GmbH) is a hydrolysis stabilizer. It can act also as a chain extender or crosslinker in polyesters, depending on the dosage and the process conditions. By reacting with carbon acid end groups in the polyester, Stabilizer 9000 "eliminates a viscosity decrease during production, or even increases the viscosity" (see information by Raschig GmbH-Stabilizer 9000 (available at raschig.com).

In hydrolysis, the ester molecule of the polymer is cleaved by the action of water to produce a carboxylic acid and an alcohol. Once initiated, this process accelerates auto-catalytically and results in complete breakdown.

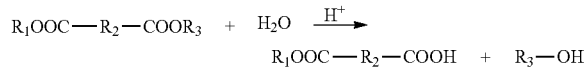

STABAXOL is an antihydrolysis agent for many polymers, including polyurethane (PU), polyethylene terephthalate (PET), polybutylene terephthalate (PBT), thermoplastic polyurethane (TPU), thermoplastic polyester elastomer (TPEE), and ethylene vinyl acetate (EVA). Polymers containing STABAXOL usually show a threefold increase in service life. When STABAXOL reacts with the cleaved products, carboxylic acid or water, it creates urea compounds that have "no negative impact on the stabilized material." (see Stabaxol_brochure_en_120330_online1 (available at rheinchemie.com).

Reaction with acid

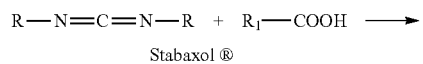
Stabaxol®

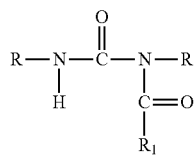

Example 6: Experimental Results

The weight average molecular weight (Mw) as a function of weeks in 65° C./50% RH aging is shown in FIG. 1 and Table 2. The Mw decrease is due to degradation by hydrolysis. The control formulation 0:0 with no HALS or HI, had a sharp decline in Mw, which fell below 60 k Daltons in less than a week and a half at 65° C./50% RH.

as a chain extender or crosslinker (Raschig GmbH—"Stabilizer 9000" (available at raschig.com). In the compounded formulations the HI at level 1 (HAL:HI levels of 0:1, 1:1, 3:1) increased the initial Mw by about 30 kDa, relative to the control. For a HI at level 3 (HALS:HI levels 0:3, 1:3, 3:3) the Mw was almost doubled. The HI alone at level 1 (HALS:HI level of 0:1) had the same sharp decline as the control formulation, but crossed the 60 kDa Mw line about two weeks later, probably due to the higher initial Mw. The HI alone at level 3 (HALS:HI level of 0:3) had a much slower decline and crossed the 60 kDa line at 20 weeks, similar to that of the PEBAX resin.

When the HALS was used alone at level 1 or 3 (HALS:HI level of 1:0 or 3:0) the Mw decline was slower than the control formulation (no HALS or HI), crossing the 60 kDa Mw line at 13 weeks at 65° C./50% RH. This indicates that HALS UV light stabilizer by itself improves the hydrolytic stability of the control formulation. One hypothesis is that the hindered tertiary amine neutralizes some chemical(s), such as acidic by-products, in the formulation that accelerate hydrolysis ("Toward tertiary amine-modulated acid-triggered hydrolysis of copolymers containing pendent ortho ester groups", Macromolecules 2013, 46, 1093-1100; US2008/0293841A1, "Polyester polyol containing polyurethane systems having improved hydrolytic stability"). This also suggests that other amines, as well as weak bases, should also work.

Combinations of HALS and HI at level 1 or 3 (level's of 1:1 or 3:1) crossed the 60 kDa Mw line at 20 weeks at 65° C./50% RH, similar to the PEBAX resin.

When the HI was used at level 3, in combination with the HALS at level 1 or 3, there was no Mw decline at 65° C./50% RH until after 10 weeks for the 1:3 level, and for at least 20 weeks for the 3:3 level. Therefore, these two HALS:HI levels of 1:3 and 3:3 stop the hydrolytic Mw degradation of the control formulation to an extent greater than the other levels of HALS:HI, either alone or in other combinations. In fact, the degradation rate of these specific additive levels in the control formulation was even less than that of the neat PEBAX polymer itself.

In summary, the hydrolytic stability with the following HALS:HI additive levels was extended to various degrees at 65° C./50% RH aging relative to the PEBAX resin, in the following order:

HALS:HI 0:0<0:1<1:0=3:0<PEBAX=1:1=3:1<0: 3<<1:3<<3:3

TABLE 2

Molecular Weight (Daltons) versus Weeks at 65° C./50% RH

*Averaged data

| HALS:HI Level | 0 | 1 | 2 | 4 | 6 | 10 | 20 |
|---|---|---|---|---|---|---|---|
| 0:0 | 120582 | 70629 | 47000 | 29489 | 22000 | 16122 | n/a |
| 0:1 | 155076 | 118156 | 81236 | 47786 | 36609 | 33000 | n/a |
| 1:0, 3:0* | 127515 | 120427 | 113339 | 104000 | 91997 | 67992 | 31300 |
| PEBAX | 127395 | 124293 | 121190 | 114000 | 105118 | 91126 | 58884 |
| 1:1, 3:1* | 172372 | 170647 | 168921 | 166089 | 154708 | 105594 | 58319 |
| 0:3 | 223592 | 213296 | 203000 | 185000 | 170000 | 139091 | 56705 |
| 1:3 | 213869 | 224131 | 234392 | 248391 | 228897 | 215902 | 155310 |
| 3:3 | 203430 | 216715 | 230000 | 246049 | 235129 | 224208 | 211904 |

Figure 2:
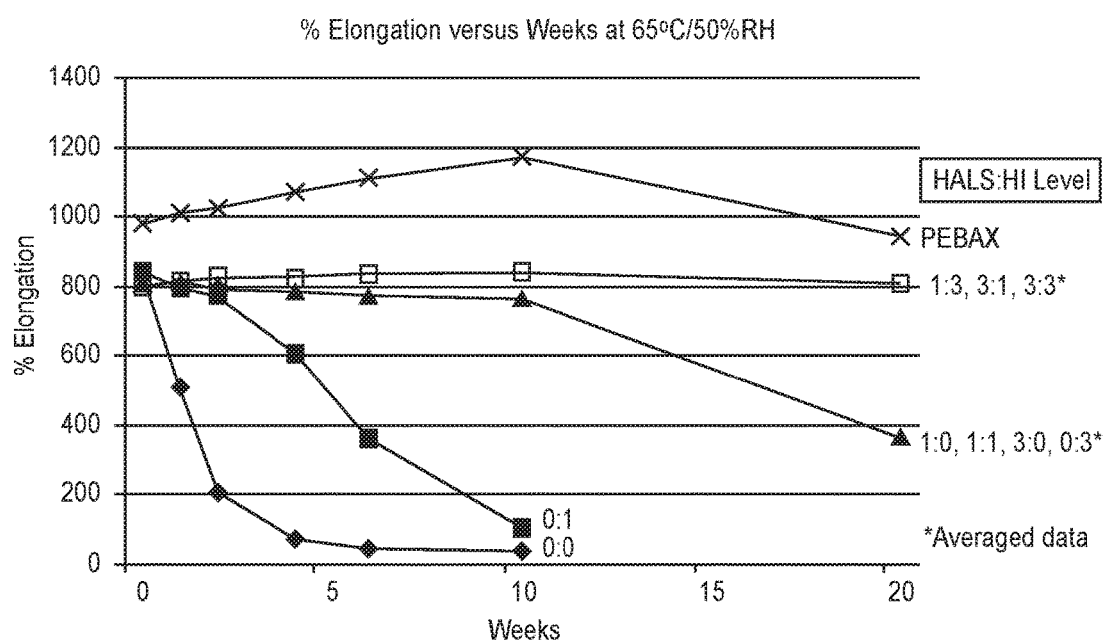
FIG. 2 is a graph of the percent elongation at break of an exemplary polymer composition with aging time at 65° C./50% RH.

Hydrolysis inhibitors can slow down hydrolytic degradation, and bring about up to a three-fold increase in polymer service life (Stabaxol_brochure_en_120330_online1 (available at rheinchemie.com). Hydrolysis inhibitors can also act The percent elongation at break as a function of aging time at 65° C./50% RH is graphed in FIG. 2 and Table 3. The initial percent elongation was not changed by the addition of the HALS and HI. The control formulation 0:0 (no HALS or HI) and the HI at level 1 (0:1 HALS:HI level) had a sharp decline in percent elongation. At levels of 1:0, 1:1, 3:0, and 0:3 there was a decline in percent elongation after 10 weeks at 65 C/50% RH. However, for the HALS:HI levels of 3:1, 1:3, and 3:3 there was no change in the percent elongation up to 20 weeks. The neat PEBAX resin also had no decline in percent elongation at 20 weeks of aging at 65 C/50% RH.

TABLE 3

Percent Elongation versus Weeks at 65° C./50% RH

| HALS:HI Level | *Averaged data | | | | | | |
|---|---|---|---|---|---|---|---|
| | 0 | 1 | 2 | 4 | 6 | 10 | 20 |
| 0:0 | 843 | 500 | 193 | 69 | 44 | 26 | n/a |
| 0:1 | 841 | 804 | 767 | 604 | 354 | 100 | n/a |
| 1:0, 1:1, 3:0, 0:3* | 802 | 796 | 789 | 780 | 775 | 760 | 361 |
| PEBAX | 981 | 1003 | 1025 | 1070 | 1115 | 1177 | 941 |
| 1:3, 3:1, 3:3* | 801 | 821 | 825 | 827 | 836 | 836 | 806 |

Figure 3:
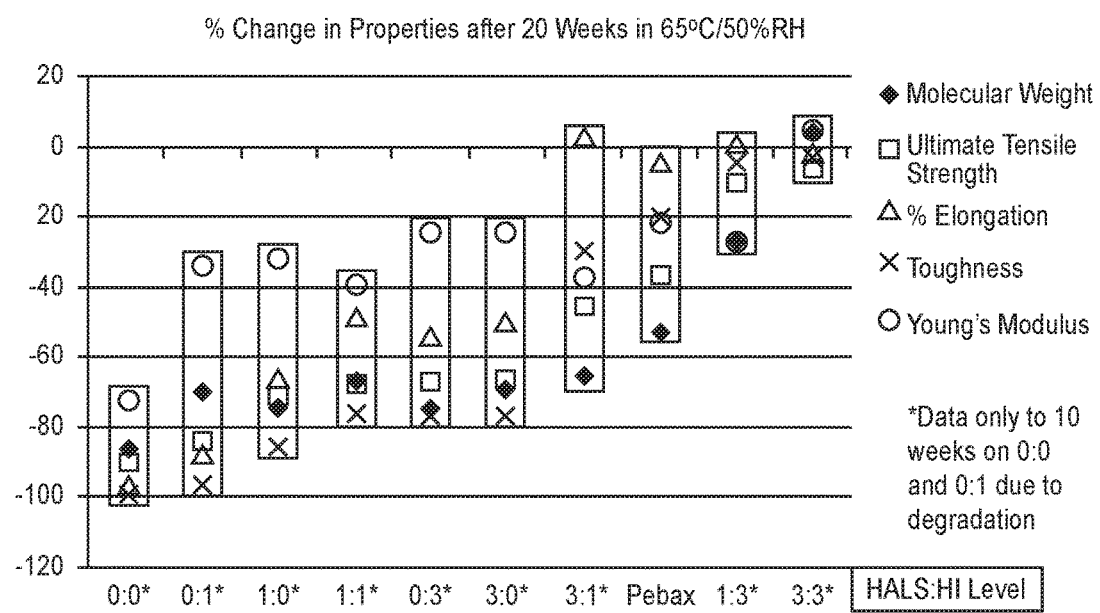
FIG. 3 is a graph of the percent change in properties of an exemplary polymer composition after 20 weeks at 65° C./50% RH.

The percent change in Mw and all mechanical properties after 20 weeks at 65° C./50% RH, relative to the initial values, is shown in FIG. 3 and Table 4. The smallest change in properties occurred for HALS and HI both at level 3 (3:3 HALS:HI levl), where the percent property change was less than that of the neat PEBAX resin. This demonstrates that the 3:3 HALS:HI level stops the hydrolytic degradation of both the Mw and corresponding mechanical properties. It is anticipated that additive combinations similar to this will also stop the hydrolytic degradation in other polymers with hydrolysable bonds, including those listed in the Stabaxol_brochure_en_120330_online1 (available at rheinchemie.com).

TABLE 4

% Change in Properties after 20 Weeks at 65° C. /50% RH

| HALS:HI Level | Molecular Weight | Ultimate Tensile Strength | % Elongation | Toughness | Young's Modulus |
|---|---|---|---|---|---|
| 0:0* | −87 | −91 | −97 | −100 | −73 |
| 0:1* | −70 | −84 | −88 | −97 | −34 |
| 1:0 | −75 | −71 | −66 | −86 | −33 |
| 1.1 | −67 | −67 | −49 | −76 | −40 |
| 0:3 | −75 | −67 | −54 | −76 | −25 |
| 3:0 | −69 | −67 | −50 | −77 | −25 |
| 3:1 | −66 | −45 | 3 | −30 | −38 |
| PEBAX | −54 | −37 | −4 | −20 | −22 |
| 1:3 | −27 | −10 | 1 | −5 | −28 |
| 3:3 | 4 | −6 | −2 | −4 | 4 |

*Data only to 10 weeks due to degradation

Example 7: Mixing

Polyether-block-amide (PEBA) resin (Type: PEBAX 2533 and 3533) was purchased from Arkema, Inc. One sample, ID 23, the PEBAX resin was ground prior to drying. The PEBAX resin was dried in a desiccant drier until the moisture content was less than 0.01% by weight. Tungsten carbide powder (WC), an antioxidant (AO) (IRGANOX 1010), a UV absorber (UVA) (TINUVIN 326), a hindered amine light stabilizer (HALS) (TINUVIN 622, CAS 65447-77-0), and a carbodiimide hydrolysis inhibitor (HI) (Stabilizer 9000, CAS 29963-44-8 and 29117-01-9) were added to the formulations based on Table 5.

The HALS and HI were evaluated at various loading levels. About fifty pounds of each formulation was made per Table 5. The additives were pre-mixed and added to the PEBAX resin to homogenize prior to compounding. The sample of neat PEBAX resin did not go through the mixing and compounding process.

TABLE 5

Formulations

Formula ID's & Descriptions

| | HALS:HI | W = WC Additive Levels (wt % to PEBAX) | Pebax | Wt % to Pebax | | | | |
|---|---|---|---|---|---|---|---|---|
| ID | Level | HALS:HI:UVA:AO | Grade | HALS | HI | UVA | AO | WC |
| 20 | 0:0 | 0011W | 3533 | 0% | 0% | 0.99% | 0.99% | 293.28% |
| 21 | 0:0 | 0011W | 3533 | 0% | 0% | 0.99% | 0.99% | 293.28% |
| 22 | 3:3 | 3311W | 3533 | 3.38% | 3.38% | 1.06% | 1.06% | 313.08% |
| 23 | 3:3 | 3311W | 3533 | 3.38% | 3.38% | 1.06% | 1.06% | 313.08% |
| 24 | 4:3 | 4311W | 3533 | 4.48% | 3.41% | 1.07% | 1.07% | 316.41% |
| 25 | 4:4 | 4411W | 3533 | 4.53% | 4.53% | 1.08% | 1.08% | 319.83% |
| 26 | 3:3 | 3311W | 2533 | 3.38% | 3.38% | 1.06% | 1.06% | 313.08% |
| 29 | 2:2 | 2211W | 3533 | 2.25% | 2.25% | 1.02% | 1.02% | 303.28% |
| 30 | 3:3 | 3311W | 3533 | 3.38% | 3.38% | 1.05% | 1.05% | 313.08% |

| Formula ID's & Descriptions | | Wt % in Formula | | | | | |
|---|---|---|---|---|---|---|---|
| ID | HALS | HI | UVA | AO | WC | Pebax | Sum |
| 20 | 0% | 0% | 0.25% | 0.25% | 74.20% | 25.30% | 100% |
| 21 | 0% | 0% | 0.25% | 0.25% | 74.20% | 25.30% | 100% |
| 22 | 0.80% | 0.80% | 0.25% | 0.25% | 74.20% | 23.70% | 100% |
| 23 | 0.80% | 0.80% | 0.25% | 0.25% | 74.20% | 23.70% | 100% |
| 24 | 1.05% | 0.80% | 0.25% | 0.25% | 74.20% | 23.45% | 100% |
| 25 | 1.05% | 1.05% | 0.25% | 0.25% | 74.20% | 23.20% | 100% |

TABLE 5-continued

| | Formulations | | | | | | |
|---|---|---|---|---|---|---|---|
| 26 | 0.80% | 0.80% | 0.25% | 0.25% | 74.20% | 23.70% | 100% |
| 29 | 0.55% | 0.55% | 0.25% | 0.25% | 74.00% | 24.40% | 100% |
| 30 | 0.80% | 0.80% | 0.25% | 0.25% | 74.20% | 23.70% | 100% |

Example 8: Compounding

The mixture for each compounded formulation was fed through a hopper into a twin screw extruder under a dry nitrogen blanket. The hot extrudate was cooled in a water bath, vacuum dried to remove surface moisture, and fed into a pelletizer. The pellets from each formulation group were dried and transferred to a polyethylene bag and sealed.

Example 9: Compression Molding Slabs

Compression molded slabs were produced as in Example 3.

Example 10: Humidity Aging and Evaluation Methods

The compounded pellets, PEBAX resin pellets, and the compression molded sheets were aged in an environmental chamber at 65° C. and humidity of 50% relative humidity (RH). The molecular weight was determined on the pellets using gel permeation chromatography (GPC). The tensile properties of dog bone samples (ASTM die D638_14 type V) were evaluated based on ASTM D638-08, using an INSTRON test system, a gauge length (extensometer) of 0.375 inch, a jaw separation of 1 inch, and a crosshead speed of 5 inches per minute. Measurements on formulations from Example 1, Table 1 were continued beyond 20 weeks and combined with formulations in Example 7, Table 5 and the data presented in FIG. 5.

Example 11: Experimental Results

Figure 5:
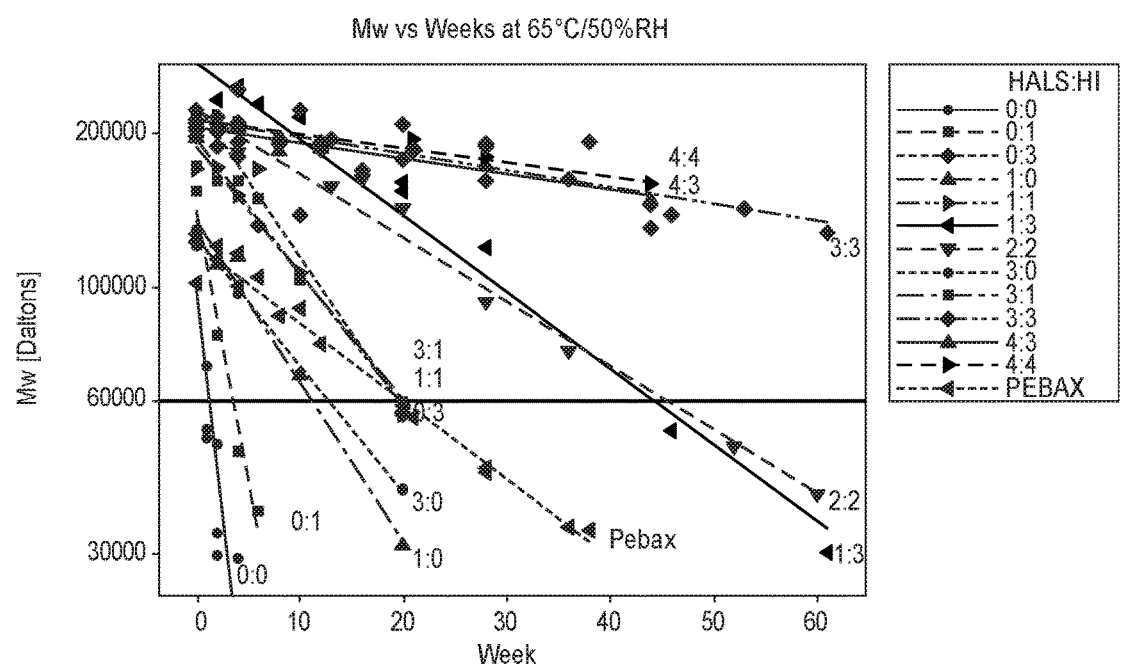
FIG. 5 is a graph of the molecular weight change of an exemplary polymer composition with aging time at 65° C./50% RH.

The weight average molecular weight (Mw) as a function of weeks in 65° C./50% RH aging is shown in FIG. 5. The Mw decrease is due to degradation by hydrolysis.

Figure 6:
FIG. 6 is a graph of the % elongation at break as a function of molecular weight of an exemplary polymer composition.

Combined with results discussed in Example 6, HALS:HI levels of 4:3, and 4:4 demonstrate that additional amounts of HALS or HI does not change the desirable result observed at level 3:3. The addition of level 2:2 provides a mid-point between levels of 1:1 and 3:3. The collection of data to 60 weeks shows continued desirable effect beyond the 20 weeks reported in Example 6. FIG. 6 is a graph of the % elongation at break vs molecular weight and demonstrates that mechanical properties are reduced when the molecular weight falls below 60,000 Daltons.

Example 12: Mixing and Compounding

Polyether-block-amide (PEBA) resin (Type: PEBAX 3533) was purchased from Arkema, Inc. The PEBAX resin was ground into a powder and dried in a desiccant drier until the moisture content was less than 0.01% by weight. Tungsten carbide powder (W), an antioxidant (AO) (IRGANOX 1010), a UV absorber (UVA) (TINUVIN 326), a carbodiimide hydrolysis inhibitor (HI) (Stabilizer 9000, CAS 29963-44-8 and 29117-01-9), a hindered amine light stabilizer (HALS) (TINUVIN 622, CAS 65447-77-0), two alternate weak bases to HALS, CHIMASORB 944 and poly(4-vinylpyridine), barium sulfate (B) as an alternate radiopaque filler, and HALS and HI at higher and lower levels, with and/or without tungsten carbide (W) were added to the formulations per Table 6. Compounding was performed the same as in Example 8. In Table 6, CHIMASORB 944 was used in sample ID 71 (denoted by 3"), and poly(4-vinylpyridine) was used in sample ID 72 (denoted by 3*).

TABLE 6

| Formulations | | | | | | | |
|---|---|---|---|---|---|---|---|
| Formula ID's and Descriptions | | | Wt % in Formula | | | | |
| ID | W = WC<br>B =<br>Ba2SO4<br>HALS:HI<br>Level | Additives Level<br>(wt % to Pebax)<br>HALS:HI:UVA:AO | HALS or alternate | HI | UVA | AO | Ba2SO4 or WC |
| 61 | 1:1 | 1111 | 1.01 | 1.01 | 1.01 | 1.01 | 0 |
| 62 | 1:2W | 1211W | 0.25 | 0.55 | 0.25 | 0.25 | 75.00 |
| 63 | 3:2W | 3211W | 0.80 | 0.55 | 0.25 | 0.25 | 74.45 |
| 64 | 2:3W | 2311W | 0.55 | 0.80 | 0.25 | 0.25 | 74.45 |
| 65 | 3:3W | 3311W | 0.80 | 0.80 | 0.25 | 0.25 | 74.20 |
| 66 | 10:10W | 101011W | 2.50 | 2.50 | 0.25 | 0.25 | 70.80 |
| 67 | 10:10 | 1010 | 8.56 | 8.56 | 0.86 | 0.86 | 0 |
| 68 | 20:20W | 202011W | 5.00 | 5.00 | 0.25 | 0.25 | 65.80 |
| 69 | 20:20 | 202011 | 14.62 | 14.62 | 0.73 | 0.73 | 0 |
| 71 | 3":3W | 3"311W | 0.80 | 0.80 | 0.25 | 0.25 | 74.20 |
| 72 | 3*:3W | 3*311W | 0.80 | 0.80 | 0.25 | 0.25 | 74.20 |
| 76 | 3:3B | 3311B | 2.17 | 2.17 | 0.68 | 0.68 | 30.02 |
| 77 | 0:0B | 0011B | 0 | 0 | 0.72 | 0.72 | 30.30 |

TABLE 6-continued

Formulations

| Formula ID's & Descriptions | Wt % in Formula | | Wt % to Pebax | | | | |
|---|---|---|---|---|---|---|---|
| ID | Pebax | Basis | HALS or alternate | HI | UVA | AO | Ba2SO4 or WC |
| 61 | 95.95 | 100 | 1.055% | 1.055% | 1.055% | 1.055% | 0% |
| 62 | 23.70 | 100 | 1.055% | 2.321% | 1.055% | 1.055% | 316% |
| 63 | 23.70 | 100 | 3.376% | 2.321% | 1.055% | 1.055% | 314% |
| 64 | 23.70 | 100 | 2.321% | 3.376% | 1.055% | 1.055% | 314% |
| 65 | 23.70 | 100 | 3.376% | 3.376% | 1.055% | 1.055% | 313% |
| 66 | 23.70 | 100 | 10.549% | 10.549% | 1.055% | 1.055% | 299% |
| 67 | 81.16 | 100 | 10.549% | 10.549% | 1.055% | 1.055% | 0% |
| 68 | 23.70 | 100 | 21.097% | 21.097% | 1.055% | 1.055% | 278% |
| 69 | 69.30 | 100 | 21.097% | 21.097% | 1.055% | 1.055% | 0% |
| 71 | 23.70 | 100 | 3.376% | 3.376% | 1.055% | 1.055% | 313% |
| 72 | 23.70 | 100 | 3.376% | 3.376% | 1.055% | 1.055% | 313% |
| 76 | 64.28 | 100 | 3.376% | 3.376% | 1.058% | 1.058% | 47% |
| 77 | 68.26 | 100 | 0% | 0% | 1.055% | 1.055% | 44% |

Example 13: Humidity Aging and Evaluation Methods

The compounded pellets and PEBAX resin pellets were aged in an environmental chamber at a higher temperature of 85° C. and 50% relative humidity (RH). The molecular weight was determined on the pellets using gel permeation chromatography (GPC).

Example 14: Experimental Results

Figure 7:
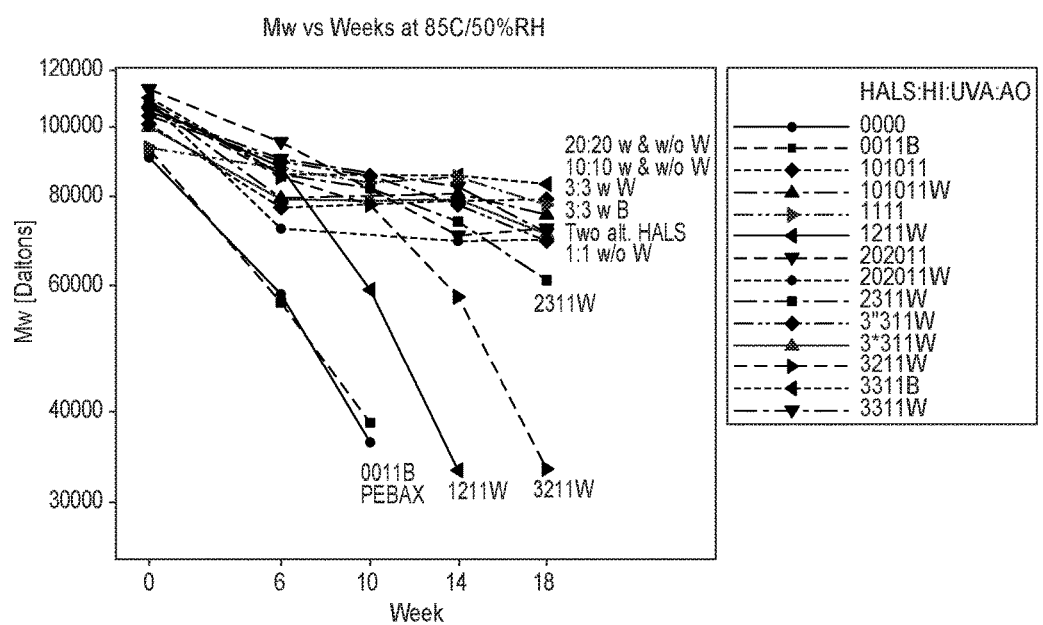
FIG. 7 is a graph of the molecular weight change of an exemplary polymer composition with aging time at 85° C./50% RH.

The weight average molecular weight (Mw) as a function of weeks in 65° C./50% RH aging is shown in FIG. 7. The Mw decrease is due to degradation by hydrolysis.

Increasing the HALS:HI levels to 10:10 and 20:20 with or without tungsten carbide, or replacing HALS with alternate weak bases CHIMISORB 944 or poly(4-vinylpyridine), or replacing tungsten-carbide with barium sulfate (B), or using a HALS:HI level 1:1 without tungsten carbide reproduce the desired result observed in HALS:HI level of 3:3. As observed in Example 11, reduced HALS:HI levels below 3:3, did not have equivalent hydrolytic stability to the HALS:HI level 3:3 formulation.

It should be noted that the molecular weight values reported in FIG. 7 were measured using a GPC system with different GPC columns, PPMA standards, and calibration methods than was used in Examples 6 and 11, which produced lower relative molecular weight values. Molecular weight collected by GPC is a relative test of the actual molecular weight of the material, and therefore may be affected by the instrument, test method, type of columns, type of detectors, etc. used to generate the result. Independent of GPC system used, GPC was able to differentiate between higher and lower molecular weight polymers which allows comparison of degradation rates.

Example 15: Mixing and Compounding

Polyether-block-amide (PEBA) resin (Type: PEBAX 3533) was purchased from Arkema, Inc. The PEBAX resin was ground into a powder and dried in a desiccant drier until the moisture content was less than 0.01% by weight. Tungsten carbide powder (WC), an antioxidant (AO) (IRGANOX 1010), a UV absorber (UVA) (TINUVIN 326), a hindered amine light stabilizer (HALS) (TINUVIN 622, CAS 65447-77-0), and a carbodiimide hydrolysis inhibitor (HI) (Stabilizer 9000, CAS 29963-44-8 and 29117-01-9) were added to the formulations per Table 7. Twenty pounds of each formulation was made per Table 7 which describes a study on five additives (HALS, HI, UVA, AO and WC).

The additives were pre-mixed and added to the PEBAX resin to homogenize prior to compounding. The sample of neat PEBAX resin did not go through the mixing or compounding process. Compounding was performed the same as in Example 8, except for sample number 42, which was compounded with higher shear for comparison to predicate processing.

TABLE 7

| Formula ID's & Descriptions | | | | | | | | | | | |
|---|---|---|---|---|---|---|---|---|---|---|---|
| W = WC | | | | | | | | | | Wt % to Pebax | |
| p = higher shear | | | Formulation Components, wt % | | | | | | | HAls | UVA |
| ID | Additives Level (wt % to Pebax) HALS:HI:UVA:AO | Pebax additives | Tinuvin 622 (HALS) | Stabilizer 9000 (HI) | Tinuvin 326 (UVA) | Irganox 1010 (AO) | Tungsten Carbide (W) | Pebax 35D | Basis 100 | or HI wt % to Pebax | or AO wt % to Pebax |
| 40 | 0011W | 3 | 0 | 0 | 0.250 | 0.250 | 73.2 | 26.300 | 100 | 0% | 0.95% |
| 41 | 0000W | 1 | 0 | 0 | 0 | 0 | 73.2 | 26.800 | 100 | 0% | 0% |
| 42 | 3311Wp | 5 | 0.800 | 0.800 | 0.250 | 0.250 | 73.2 | 24.700 | 100 | 3.24% | 1.01% |
| 43 | 3311W | 5 | 0.800 | 0.800 | 0.250 | 0.250 | 73.2 | 24.700 | 100 | 3.24% | 1.01% |
| 44 | 3310W | 4 | 0.808 | 0.808 | 0.252 | 0 | 73.2 | 24.932 | 100 | 3.24% | 1.01% |
| 45 | 3301W | 4 | 0.808 | 0.808 | 0 | 0.252 | 73.2 | 24.932 | 100 | 3.24% | 1.01% |

TABLE 7-continued

Formula ID's & Descriptions

W = WC
p = higher shear

| ID | Additives Level (wt % to Pebax) HALS:HI:UVA:AO | Pebax additives | Tinuvin 622 (HALS) | Stabilizer 9000 (HI) | Tinuvin 326 (UVA) | Irganox 1010 (AO) | Tungsten Carbide (W) | Pebax 35D | Basis 100 | HAls or HI wt % to Pebax | UVA or AO wt % to Pebax |
|---|---|---|---|---|---|---|---|---|---|---|---|
| 46 | 3300W | 3 | 0.815 | 0.815 | 0 | 0 | 73.2 | 25.170 | 100 | 3.24% | 0% |
| 47 | 3311 | 4 | 2.987 | 2.987 | 0.933 | 0.933 | 0 | 92.160 | 100 | 3.24% | 1.01% |
| 48 | 3310 | 3 | 3.013 | 3.013 | 0.940 | 0 | 0 | 93.034 | 100 | 3.24% | 1.01% |
| 49 | 3301 | 3 | 3.013 | 3.013 | 0 | 0.940 | 0 | 93.034 | 100 | 3.24% | 1.01% |
| 50 | 3300 | 2 | 3.042 | 3.042 | 0 | 0 | 0 | 93.916 | 100 | 3.24% | 0% |
| 51 | 3010 | 2 | 3.109 | 0 | 0.970 | 0 | 0 | 95.921 | 100 | 3.24% | 1.01% |
| 52 | 0310 | 2 | 0 | 3.109 | 0.970 | 0 | 0 | 95.921 | 100 | 3.24% | 1.01% |
| 53 | 0011 | 2 | 0 | 0 | 0.990 | 0.990 | 0 | 98.020 | 100 | 0% | 1.01% |
| 54 | 0300 | 1 | 0 | 3.137 | 0 | 0 | 0 | 96.863 | 100 | 3.24% | 0% |
| 55 | 3000 | 1 | 3.137 | 0 | 0 | 0 | 0 | 96.863 | 100 | 3.24% | 0% |
| 56 | 0010 | 1 | 0 | 0 | 1.000 | 0 | 0 | 99.000 | 100 | 0% | 1.01% |
| 57 | 0000 | 0 | 0 | 0 | 0 | 0 | 0 | 100 | 100 | 0% | 0% |

Example 16: Humidity Aging and Evaluation Methods

The compounded pellets and the PEBAX resin pellets were aged in environmental chambers at 85° C. with 50% relative humidity (RH). The molecular weight was determined on the pellets using gel permeation chromatography (GPC).

Example 17: Experimental Results

Figure 8A:
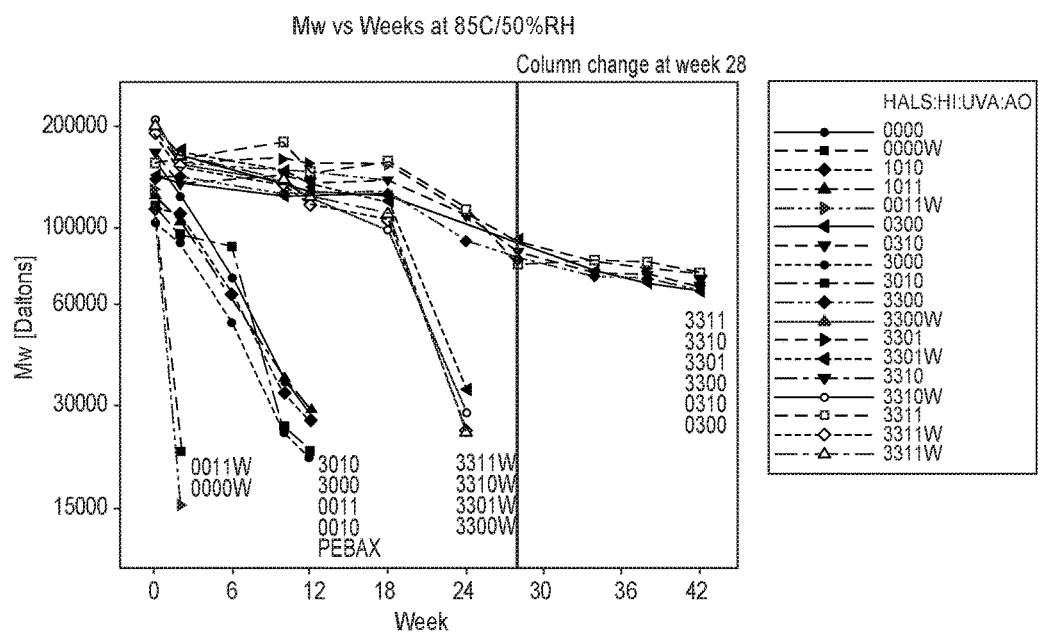
FIGS. 8a and 8b are graphs of the molecular weight change of an exemplary polymer composition with aging time at 85° C./50% RH.
Figure 8B:
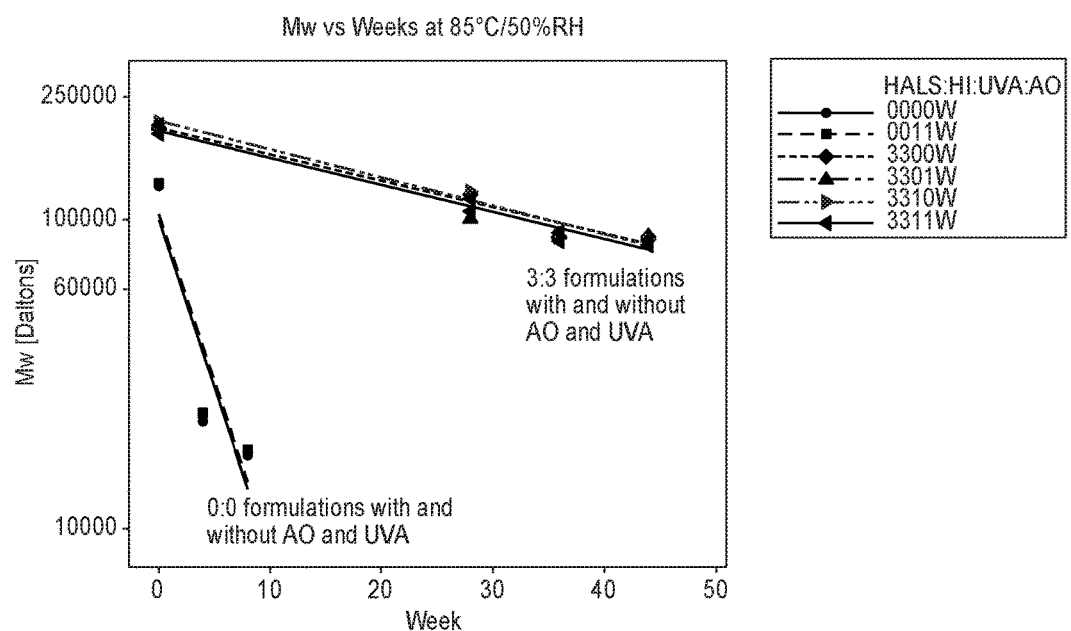

The weight average molecular weight (Mw) as a function of weeks in 85° C./50% RH aging is shown in FIGS. 8a and 8b. The Mw decrease is due to degradation by hydrolysis.

FIG. 8a is a graph of the effect of all 5 additives on the hydrolytic stability of PEBAX. It should be noted that the molecular weight values reported on and after week 28 were measured using a GPC system with different GPC columns, PPMA standards, and calibration methods than previous Examples, which produced lower relative molecular weight values. Molecular weight collected by GPC is a relative test of the actual molecular weight of the material, and therefore may be affected by the instrument, test method, type of columns, type of detectors, etc. used to generate the result.

FIG. 8b is a subset of the samples in FIG. 8a, containing tungsten-carbide, and demonstrates that the desirable result exemplified in Examples 6 and 11 is not dependent on the anti-oxidant (AO) or ultra-violet absorber (UVA) included in any previous Examples.

Example 18: Experimental Results

Material from Example 4 aged for 10 weeks (for level 0:0) and 20 weeks (for levels 3:0, 0:3, and 3:3) was further studied using $^{13}C$ Nuclear Magnetic Resonance (NMR).

Figure 9:
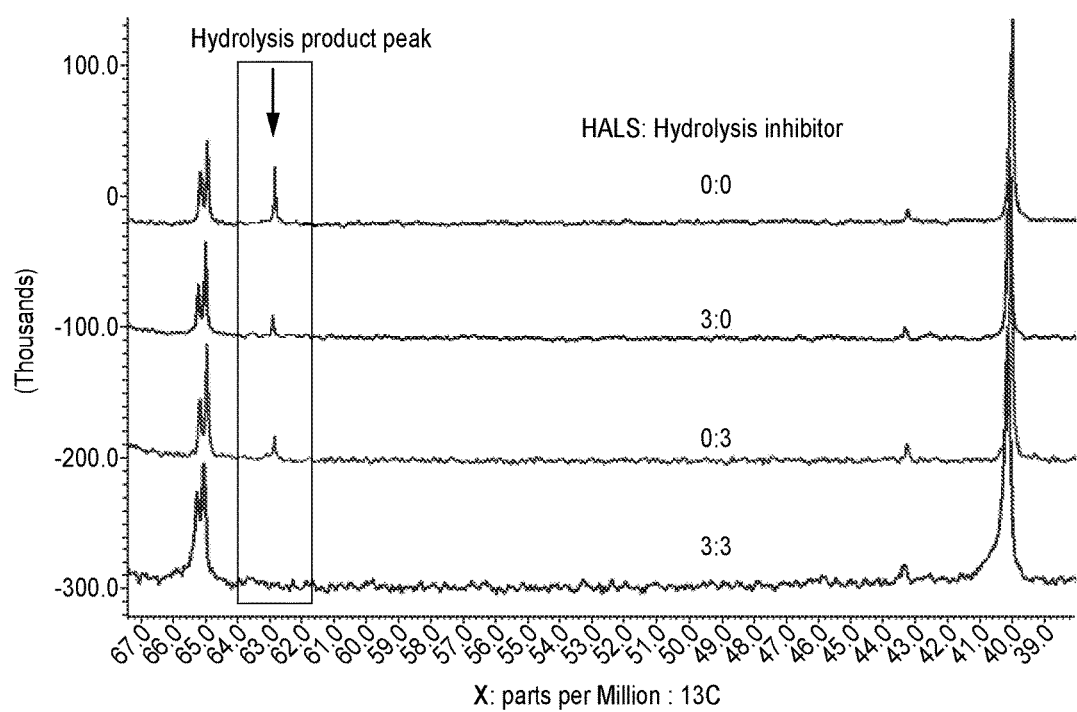
FIG. 9 is a graph of $^{13}$C Nuclear Magnetic Resonance spectra of an exemplary polymer composition.

The NMR spectra in FIG. 9 shows a hydrolytic degradation byproduct in the HALS:HI level 0:0 within 10 weeks of aging. The degradation observed is due to the hydrolysis of the ester bond linkage in the PEBAX resin, indicated by the peak at 62-63 ppm which detects $CH_2$ groups next to hydroxyl groups that are a result of hydrolysis.

When HALS and HI additives were added at the level of 3:0 and 0:3, hydrolysis of PEBAX resin was suppressed, as indicated by a smaller degradation product peak at a longer aging time (20 weeks). The NMR data show that HALS or HI alone (levels 3:0 and 0:3) cannot prevent hydrolysis completely. However, the data show that a combination of HALS and HI at levels 3:3 HALS:HI prevented hydrolysis of PEBAX for a demonstrated 20 weeks in 65 C/50% RH aging.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed:

1. A composition comprising:
   a polymer comprising a polyether or a polyether block amide;
   a polymeric carbodiimide compound in an amount of at least 0.25 wt-% and up to 14.6 wt-%, based on the total weight of the composition; and
   a hindered amine in an amount of at least 0.25 wt-% and up to 14.6 wt-%, based on the total weight of the composition;
   wherein the polymeric carbodiimide compound comprises:
   a 2,6- or 2,4,6-isopropyl substituted aromatic polycarbodiimide having a number average molecular weight of 1,000 g/mol to 50,000 g/mol; or
   a sterically hindered polymeric carbodiimide represented by the formula:

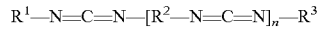

wherein:
   n is up to 1000;
   $R^1$ and $R^3$ individually represent a monovalent aliphatic group having 1 to 40 carbon atoms, a cycloaliphatic group having 6 to 40 carbon atoms, an aromatic group having 6 to 40 carbon atoms, or combinations thereof; and
   $R^2$ represents a divalent aliphatic group having 1 to 40 carbon atoms, a cycloaliphatic group having 6 to 40 carbon atoms, an aromatic group having 6 to 40 carbon atoms, or combinations thereof;
wherein the hindered amine comprises a compound of formulas (III) or (IV):

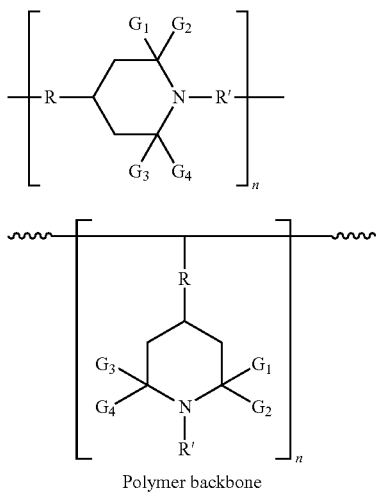

wherein:
R' represents hydrogen, oxy, hydroxy, alkyl of 1 to 18 carbon atoms, alkenyl of 3 to 18 carbon atoms, aralkyl of 7 to 9 carbon atoms, cycloalkyl of 5 to 12 carbon atoms, hydroxy alkyl of 2 to 6 carbon atoms, alkoxy alkyl of 2 to 20 carbon atoms, alkanoyl of 1 to 18 carbon atoms, alkoxy of 1 to 18 carbon atoms, cycloalkoxy of 5 to 12 carbon atoms, aryloxy of 6 to 10 carbon atoms, hydroxyalkoxy of 2 to 6 carbon atoms, alkoxyalkoxy of 2 to 20 carbon atoms, aralkoxy of 7 to 15 carbon atoms, or bicyclo or nicycloaliphatic oxy radical of 7 to 12 carbon atoms;

G1, G2, G3, and G4 each independently represents an alkyl group of 1 to 4 carbon atoms, or G1 and G2 and/or G3 and G4 together are pentamethylene;

R represents a divalent organic group; and n represents a number of repeat units; or the hindered amine comprises:

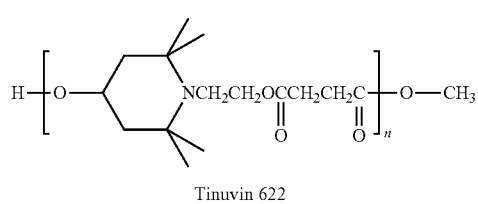
Tinuvin 622

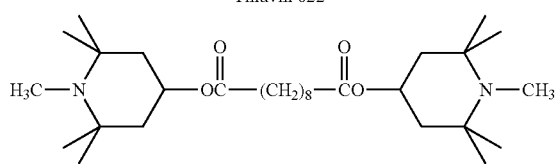
Tinuvin 765

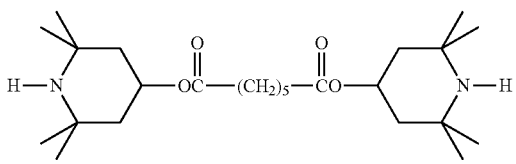
Tinuvin 770

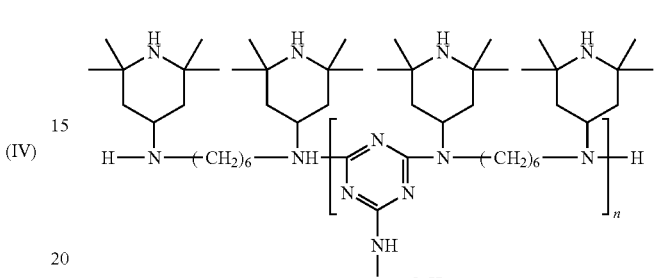
CHIMASSORB 944

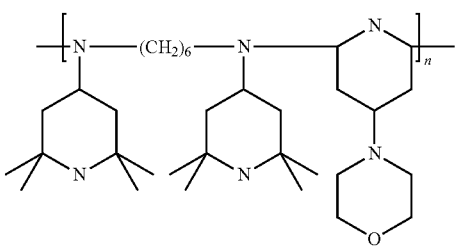
Cyasorb UV3346

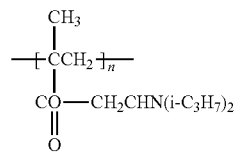
DPA-EMA wherein n represents a number of repeat units in each polymer;
wherein the composition does not include a mixture of a polymeric carbodiimide compound and a monomeric or oligomeric carbodiimide compound.

2. The composition of claim 1 which forms all or part of a final article.

3. The composition of claim 2 wherein the final article is a medical device.

4. The composition of claim 1 further comprising a filler.

5. The composition of claim 4 wherein the filler comprises a metal, metal alloy, metal-containing compound, a silica-containing compound, or combinations thereof.

6. The composition of claim 5 wherein the filler comprises tungsten carbide, barium sulfate, silver, tungsten, tantalum, bismuth, platinum-iridium alloy, bismuth subcarbonate, bismuth trioxide, bismuth oxychloride, glass, or combinations thereof.

7. The composition of claim 6 wherein the filler comprises tungsten carbide powder.

8. The composition of claim 1 wherein the polymeric carbodiimide compound comprises a 2,6- or 2,4,6-isopropyl substituted aromatic polycarbodiimide having a number average molecular weight of 1,000 g/mol to 50,000 g/mol.

9. The composition of claim 8 wherein the polymeric carbodiimide compound is represented by the formula (I):

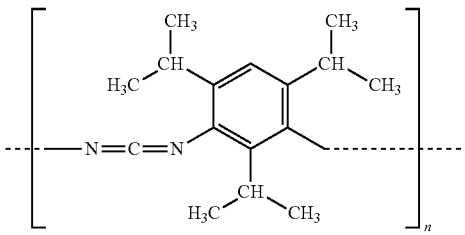

wherein n represents a number of repeat units.

10. The composition of claim 1 wherein the polymeric carbodiimide compound comprises a sterically hindered polymeric carbodiimide represented by the formula:

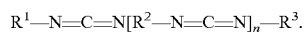

11. The composition of claim 1 wherein the hindered amine comprises:

wherein n represents a number of repeat units in each polymer.

12. The composition of claim 11 wherein the hindered amine comprises:

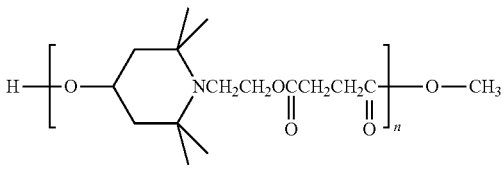

Tinuvin 622

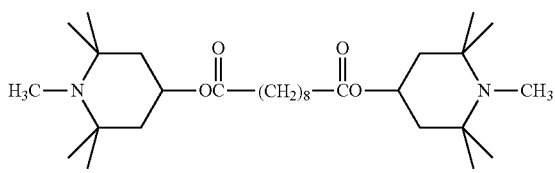

Tinuvin 765

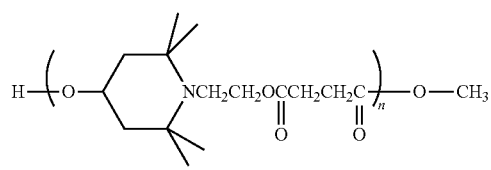

Tinuvin 622

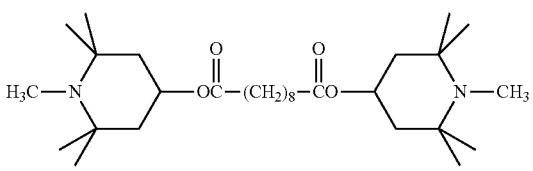

Tinuvin 765

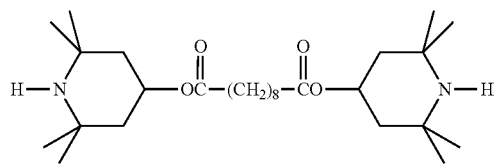

Tinuvin 770

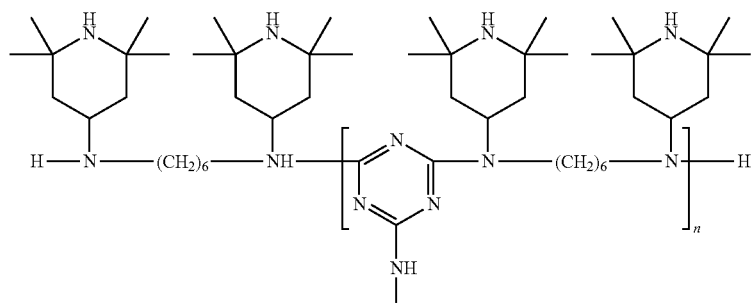

CHIMASSORB 944

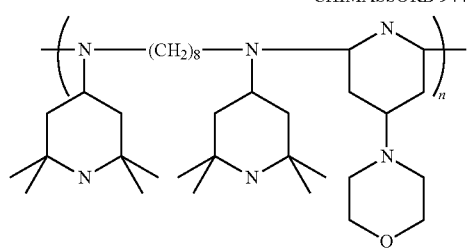

Cyasorb UV3346

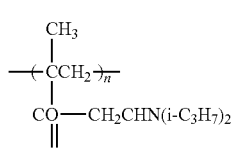

DPA-EMA

-continued

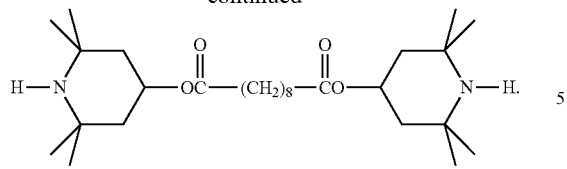

Tinuvin 770

13. The composition of claim 1 further comprising one or more additives selected from a light stabilizer, antioxidant, radiopaque agent, echogenetic agent, lubricious agent, colorant, antistatic agent, tackifier, flame retardant, matting agent, and combinations thereof.

14. The composition of claim 13 comprising a UV light stabilizer, an antioxidant, or a combination thereof.

15. The composition of claim 1 wherein the hindered amine comprises one or more compounds of the formulas (III) or (IV).

16. An article comprising the composition of claim 1.

17. The article of claim 16 which is a medical device.

* * * * *